US012703879B2

(12) United States Patent
Qian et al.

(10) Patent No.: US 12,703,879 B2
(45) **Date of Patent: *Aug. 11, 2026**

(54) RNASE H ASSISTED IN SITU ROLLING CIRCLE AMPLIFICATION

(71) Applicant: 10x Genomics, Inc., Pleasanton, CA (US)

(72) Inventors: Yufeng Qian, Pleasanton, CA (US); Shankar Shastry, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 501 days.

This patent is subject to a terminal disclaimer.

(21) Appl. No.: 18/127,582

(22) Filed: Mar. 28, 2023

(65) Prior Publication Data

US 2023/0374573 A1 Nov. 23, 2023

Related U.S. Application Data

(60) Provisional application No. 63/325,088, filed on Mar. 29, 2022.

(51) Int. Cl.

| | |
|---|---|
| ***C12Q 1/68*** | (2018.01) |
| ***C12N 9/22*** | (2006.01) |
| ***C12Q 1/44*** | (2006.01) |
| ***C12Q 1/6844*** | (2018.01) |

(52) U.S. Cl.

CPC ............. *C12Q 1/6844* (2013.01); *C12N 9/22* (2013.01); *C12Q 1/44* (2013.01); *C12Y 301/26004* (2013.01)

(58) Field of Classification Search

None

See application file for complete search history.

(56) References Cited

U.S. PATENT DOCUMENTS

| | | | |
|---|---|---|---|
| 4,318,846 | A | 3/1982 | Khanna et al. |
| 4,683,195 | A | 7/1987 | Mullis et al. |
| 4,683,202 | A | 7/1987 | Mullis |
| 4,757,141 | A | 7/1988 | Fung et al. |
| 4,800,159 | A | 1/1989 | Mullis et al. |
| 4,849,336 | A | 7/1989 | Miyoshi et al. |
| 4,965,188 | A | 10/1990 | Mullis et al. |
| 5,066,580 | A | 11/1991 | Lee |
| 5,073,562 | A | 12/1991 | Djuric et al. |
| 5,091,519 | A | 2/1992 | Cruickshank |
| 5,151,507 | A | 9/1992 | Hobbs et al. |
| 5,188,934 | A | 2/1993 | Menchen |
| 5,198,537 | A | 3/1993 | Huber et al. |
| 5,344,757 | A | 9/1994 | Holtke et al. |
| 5,354,657 | A | 10/1994 | Boehringer et al. |
| 5,366,860 | A | 11/1994 | Bergot et al. |
| 5,512,462 | A | 4/1996 | Cheng |
| 5,599,675 | A | 2/1997 | Brenner |
| 5,635,352 | A | 6/1997 | Urdea et al. |
| 5,688,648 | A | 11/1997 | Mathies |
| 5,695,940 | A | 12/1997 | Drmanac et al. |
| 5,702,888 | A | 12/1997 | Holtke et al. |
| 5,750,341 | A | 5/1998 | Macevicz |
| 5,800,996 | A | 9/1998 | Lee et al. |
| 5,847,162 | A | 12/1998 | Lee et al. |
| 5,990,479 | A | 11/1999 | Weiss et al. |
| 6,172,218 | B1 | 1/2001 | Brenner |
| 6,207,392 | B1 | 3/2001 | Weiss et al. |
| 6,251,303 | B1 | 6/2001 | Bawendi et al. |
| 6,265,552 | B1 | 7/2001 | Schatz |
| 6,306,597 | B1 | 10/2001 | Macevicz |
| 6,319,426 | B1 | 11/2001 | Bawendi et al. |
| 6,322,901 | B1 | 11/2001 | Bawendi et al. |
| 6,391,937 | B1 | 5/2002 | Beuhler et al. |
| 6,423,551 | B1 | 7/2002 | Weiss et al. |
| 6,426,513 | B1 | 7/2002 | Bawendi et al. |
| 6,444,143 | B2 | 9/2002 | Bawendi et al. |
| 6,534,266 | B1 | 3/2003 | Singer |
| 6,576,291 | B2 | 6/2003 | Bawendi et al. |
| 6,969,488 | B2 | 11/2005 | Bridgham et al. |
| 7,057,026 | B2 | 6/2006 | Barnes et al. |
| 7,255,994 | B2 | 8/2007 | Lao |
| 7,264,929 | B2 | 9/2007 | Rothberg et al. |
| 7,345,159 | B2 | 3/2008 | Ju et al. |
| 7,473,767 | B2 | 1/2009 | Dimitrov |
| 7,534,991 | B2 | 5/2009 | Miller et al. |
| 7,544,794 | B1 | 6/2009 | Benner |

(Continued)

FOREIGN PATENT DOCUMENTS

| | | | |
|---|---|---|---|
| EP | 4015647 | A1 | 6/2022 |
| WO | WO 1991/017160 | | 11/1991 |

(Continued)

OTHER PUBLICATIONS

Archer et al., "Selective and flexible depletion of problematic sequences from RNA-seq libraries at the cDNA stage," BMC Genomics. (2014) 15(1):401.

Bibikova et al., "Quantitative gene expression profiling in formalin-fixed, paraffin-embedded tissues using universal bead arrays," Am J Pathol. Nov. 2004;165(5):1799-807.

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

Chen et al., "Nanoscale imaging of RNA with expansion microscopy," Nat Methods. (2016) 13:679-684.

Chen et al., "Expansion Microscopy," Science (2015) 347(6221):543-548.

(Continued)

*Primary Examiner* — Suryaprabha Chunduru

(74) *Attorney, Agent, or Firm* — WILSON SONSINI GOODRICH & ROSATI

(57) ABSTRACT

The present disclosure relates in some aspects to methods for analyzing a target RNA in a biological sample, such as detection of a sequence of interest in an RNA. In some aspects, provided herein are methods of using an RNase such as RNase H to provide in situ RNA detection methods having high sensitivity, efficiency, and/or specificity.

19 Claims, 10 Drawing Sheets

(56) References Cited

U.S. PATENT DOCUMENTS 7,555,155 B2 6/2009 Levenson et al.
7,566,537 B2 7/2009 Balasubramanian et al.
7,655,898 B2 2/2010 Miller
7,893,227 B2 2/2011 Wu et al.
7,910,304 B2 3/2011 Drmanac
7,914,987 B2 3/2011 Fredriksson et al.
7,941,279 B2 5/2011 Hwang et al.
7,989,166 B2 8/2011 Koch et al.
8,124,751 B2 2/2012 Pierce et al.
8,133,672 B2 3/2012 Bjornson et al.
8,199,999 B2 6/2012 Hoyt et al.
8,257,954 B2 9/2012 Clark et al.
8,268,554 B2 9/2012 Schallmeiner
8,330,087 B2 12/2012 Domenicali
8,343,746 B2 1/2013 Rank et al.
8,415,102 B2 4/2013 Geiss et al.
8,431,691 B2 4/2013 McKernan et al.
8,460,865 B2 6/2013 Chee et al.
8,462,981 B2 6/2013 Determan et al.
8,481,258 B2 7/2013 Church et al.
8,519,115 B2 8/2013 Webster et al.
8,551,710 B2 10/2013 Bernitz et al.
8,562,989 B2 10/2013 Jakobovits et al.
8,580,504 B2 11/2013 Fredriksson et al.
8,632,975 B2 1/2014 Vander Horn et al.
8,658,361 B2 2/2014 Wu et al.
8,658,365 B2 2/2014 Bjornson et al.
8,771,950 B2 7/2014 Church et al.
8,921,086 B2 12/2014 Hanzel et al.
8,986,926 B2 3/2015 Ferree et al.
9,201,063 B2 12/2015 Sood et al.
9,217,178 B2 12/2015 Fedurco et al.
9,273,349 B2 3/2016 Nguyen et al.
9,279,155 B2 3/2016 Bjornson et al.
9,371,563 B2 6/2016 Geiss et al.
9,371,598 B2 6/2016 Chee
9,376,717 B2 6/2016 Gao et al.
9,512,422 B2 12/2016 Barnard et al.
9,541,504 B2 1/2017 Hoyt
9,551,032 B2 1/2017 Landegren et al.
9,624,538 B2 4/2017 Church et al.
9,650,406 B2 5/2017 Zhou et al.
9,714,446 B2 7/2017 Webster et al.
9,714,937 B2 7/2017 Dunaway
9,727,810 B2 8/2017 Fodor et al.
9,778,155 B2 10/2017 Gradinaru et al.
9,783,841 B2 10/2017 Nolan et al.
9,889,422 B2 2/2018 Smith et al.
9,909,167 B2 3/2018 Samusik et al.
10,032,064 B2 7/2018 Hoyt
10,059,990 B2 8/2018 Boyden et al.
10,126,242 B2 11/2018 Miller et al.
10,138,509 B2 11/2018 Church et al.
10,179,932 B2 1/2019 Church et al.
10,227,639 B2 3/2019 Levner et al.
10,246,700 B2 4/2019 Dunaway et al.
10,253,311 B2 4/2019 Doudna et al.
10,266,888 B2 4/2019 Daugharthy et al.
10,267,808 B2 4/2019 Cai
10,309,879 B2 6/2019 Chen et al.
10,317,321 B2 6/2019 Tillberg et al.
10,364,457 B2 7/2019 Wassie et al.
10,370,698 B2 8/2019 Nolan et al.
10,415,080 B2 9/2019 Dunaway et al.
10,457,980 B2 10/2019 Cai et al.
10,465,235 B2 11/2019 Gullberg et al.
10,494,662 B2 12/2019 Church et al.
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,526,649 B2 1/2020 Chen et al.
10,545,075 B2 1/2020 Deisseroth et al.
10,550,429 B2 2/2020 Harada et al.
10,580,128 B2 3/2020 Miller
10,640,816 B2 5/2020 Beechem et al.
10,640,826 B2 5/2020 Church et al.
10,655,176 B2 5/2020 Stromberg et al.
10,669,569 B2 6/2020 Gullberg et al.
10,746,981 B2 8/2020 Tomer et al.
10,768,173 B1 9/2020 Arslan et al.
10,774,372 B2 9/2020 Chee et al.
10,774,374 B2 9/2020 Frisén et al.
10,794,802 B2 10/2020 Gradinaru et al.
10,802,262 B2 10/2020 Tomer et al.
10,815,519 B2 10/2020 Husain et al.
10,829,814 B2 11/2020 Fan et al.
10,844,426 B2 11/2020 Daugharthy et al.
10,858,698 B2 12/2020 Church et al.
10,872,679 B2 12/2020 Cai et al.
10,964,001 B2 3/2021 Miller
11,174,281 B1 11/2021 Graham et al.
11,287,422 B2 3/2022 Previte et al.
11,434,525 B2 9/2022 Glezer
11,459,603 B2 10/2022 Tyagi et al.
11,499,185 B2 11/2022 Vijayan et al.
11,643,679 B2 5/2023 Glezer et al.
11,761,001 B2 9/2023 Ma et al.
11,999,999 B2 6/2024 Ju et al.
12,139,751 B2 11/2024 Qian et al.
12,319,956 B2 6/2025 Wang et al.
2002/0045045 A1 4/2002 Adams et al.
2003/0017264 A1 1/2003 Treadway et al.
2005/0100900 A1 5/2005 Kawashima et al.
2005/0164234 A1 7/2005 Crooke et al.
2006/0188901 A1 8/2006 Barnes et al.
2006/0240439 A1 10/2006 Smith et al.
2006/0281109 A1 12/2006 Barr et al.
2007/0166705 A1 7/2007 Milton et al.
2009/0118128 A1 5/2009 Liu et al.
2010/0055733 A1 3/2010 Lutolf et al.
2011/0005986 A1 1/2011 Kelly et al.
2011/0059865 A1 3/2011 Smith et al.
2011/0223585 A1 9/2011 Gullberg et al.
2012/0270305 A1 10/2012 Reed et al.
2013/0079232 A1 3/2013 Kain et al.
2013/0260372 A1 10/2013 Buermann et al.
2013/0288249 A1 10/2013 Gullbert
2013/0323729 A1 12/2013 Landegren et al.
2014/0120534 A1* 5/2014 Bernitz ................ C12Q 1/6809
435/6.11
2016/0024555 A1 1/2016 Church et al.
2016/0108458 A1 4/2016 Frei et al.
2016/0289734 A1 10/2016 Zamore et al.
2016/0305856 A1 10/2016 Boyden et al.
2016/0369329 A1 12/2016 Cai et al.
2016/0376642 A1 12/2016 Landegren et al.
2017/0009278 A1 1/2017 Söderberg et al.
2017/0081489 A1 3/2017 Rodriques et al.
2017/0101672 A1 4/2017 Luo et al.
2017/0219465 A1 8/2017 Desseroth et al.
2017/0220733 A1 8/2017 Zhuang et al.
2017/0253918 A1 9/2017 Kohman
2018/0052081 A1 2/2018 Kohman
2018/0080876 A1 3/2018 Rockel et al.
2018/0208967 A1 7/2018 Larman et al.
2018/0237864 A1 8/2018 Imler et al.
2018/0251833 A1 9/2018 Daugharthy et al.
2018/0320226 A1 11/2018 Church et al.
2018/0327818 A1 11/2018 Landegren et al.
2019/0017106 A1 1/2019 Frisen et al.
2019/0032121 A1 1/2019 Daugharthy et al.
2019/0032128 A1 1/2019 Chen et al.
2019/0055594 A1 2/2019 Samusik et al.
2019/0112599 A1 4/2019 Church et al.
2019/0119735 A1 4/2019 Deisseroth et al.
2019/0144940 A1 5/2019 Landegren et al.
2019/0155835 A1 5/2019 Daugharthy et al.
2019/0161796 A1 5/2019 Hauling et al.
2019/0177718 A1 6/2019 Church et al.
2019/0177800 A1 6/2019 Boutet et al.
2019/0194709 A1 6/2019 Church et al.
2019/0218608 A1 7/2019 Daugharthy et al.
2019/0249248 A1 8/2019 Beechem et al.

(56) References Cited

U.S. PATENT DOCUMENTS

2019/0264270 A1 8/2019 Zhuang et al.
2019/0271028 A1 9/2019 Khafizov et al.
2019/0276881 A1 9/2019 Zhuang et al.
2019/0339203 A1 11/2019 Miller et al.
2019/0367969 A1 12/2019 Belhocine
2020/0010891 A1 1/2020 Beechem et al.
2020/0071751 A1 3/2020 Daugharthy et al.
2020/0123597 A1 4/2020 Daniel
2020/0140920 A1 5/2020 Pierce et al.
2020/0224243 A1 7/2020 Desai et al.
2020/0224244 A1* 7/2020 Nilsson .................. C12Q 1/682
2020/0239946 A1 7/2020 Dewal
2020/0354774 A1 11/2020 Church et al.
2020/0354782 A1 11/2020 Dewal
2020/0362398 A1 11/2020 Kishi et al.
2020/0393343 A1 12/2020 Kennedy-Darling et al.
2021/0017587 A1 1/2021 Cai et al.
2021/0115504 A1 4/2021 Cai et al.
2021/0164039 A1 6/2021 Wang et al.
2021/0198727 A1 7/2021 Kühnemund et al.
2021/0238662 A1 8/2021 Bava
2021/0238674 A1 8/2021 Bava
2021/0254140 A1 8/2021 Stahl et al.
2021/0262018 A1 8/2021 Bava et al.
2021/0277460 A1 9/2021 Bava
2021/0340618 A1 11/2021 Kühnemund et al.
2021/0340621 A1 11/2021 Daugharthy et al.
2021/0388423 A1 12/2021 Bava et al.
2021/0388424 A1 12/2021 Bava
2022/0049302 A1 2/2022 Daugharthy et al.
2022/0049303 A1 2/2022 Busby et al.
2022/0083832 A1 3/2022 Shah
2022/0084628 A1 3/2022 Shah
2022/0084629 A1 3/2022 Shah
2022/0136049 A1 5/2022 Bava et al.
2022/0186254 A1 6/2022 Ma et al.
2022/0186300 A1 6/2022 Bava
2022/0195498 A1 6/2022 Kuhnemund et al.
2022/0213529 A1 7/2022 Kuhnemund et al.
2022/0228200 A1 7/2022 Bava
2022/0235403 A1 7/2022 Costa
2022/0282306 A1 9/2022 Bava
2022/0282316 A1 9/2022 Bava
2022/0282319 A1 9/2022 Verheyen
2022/0372570 A1 11/2022 Costa
2022/0380838 A1 12/2022 Qian
2022/0403458 A1 12/2022 Bava
2023/0002808 A1 1/2023 Mignardi
2023/0012607 A1 1/2023 Kühnemund et al.
2023/0013775 A1 1/2023 Chen et al.
2023/0015226 A1 1/2023 Chen et al.
2023/0026886 A1 1/2023 Chen
2023/0031305 A1 2/2023 Verheyen
2023/0031996 A1 2/2023 Qian et al.
2023/0035685 A1 2/2023 Qian et al.
2023/0037182 A1 2/2023 Bava et al.
2023/0039148 A1 2/2023 Verheyen
2023/0041485 A1 2/2023 Marks
2023/0044650 A1 2/2023 Dockter
2023/0057571 A1 2/2023 Costa et al.
2023/0061542 A1 3/2023 Kühnemund
2023/0084407 A1 3/2023 Hernández Neuta et al.
2023/0115903 A1 4/2023 Hernández Neuta et al.
2023/0159997 A1 5/2023 Belhocine et al.
2023/0160794 A1 5/2023 Dockter et al.
2023/0183787 A1 6/2023 Bava et al.
2023/0235306 A1 7/2023 Ma et al.
2023/0242974 A1 8/2023 Costa et al.
2023/0279465 A1 9/2023 He et al.
2023/0279475 A1 9/2023 Kuhnemund et al.
2023/0279480 A1 9/2023 Kühnemund
2023/0287478 A1 9/2023 Bava
2023/0314327 A1 10/2023 Hoffman
2023/0314328 A1 10/2023 Costa
2023/0323427 A1 10/2023 Schnall-Levin
2023/0323430 A1 10/2023 Shastry
2023/0323437 A1 10/2023 Chen et al.
2023/0374580 A1 11/2023 Costa
2023/0416821 A1 12/2023 Bava et al.
2024/0002902 A1 1/2024 Jakobsen et al.
2024/0026426 A1 1/2024 Bava
2024/0026427 A1 1/2024 Kuhnemund
2024/0026439 A1 1/2024 Sasaki
2024/0026448 A1 1/2024 Costa
2024/0035070 A1 2/2024 Christopherson
2024/0035071 A1 2/2024 Delaney et al.
2024/0035072 A1 2/2024 Christopherson
2024/0043910 A1 2/2024 Shastry
2024/0043914 A1 2/2024 Chen et al.
2024/0060119 A1 2/2024 Bava
2024/0084373 A1 3/2024 Shastry
2024/0084378 A1 3/2024 Marks et al.
2024/0101978 A1 3/2024 Boghospor et al.
2024/0132938 A1 4/2024 Kühnemund
2024/0141418 A1 5/2024 Mielinis
2024/0150816 A1 5/2024 Feng et al.
2024/0158852 A1 5/2024 Belhocine et al.
2024/0167081 A1 5/2024 Bava et al.
2024/0175082 A1 5/2024 Costa
2024/0175083 A1 5/2024 Bava et al.
2024/0191297 A1 6/2024 Christopherson et al.
2024/0209330 A1 6/2024 Shastry et al.
2024/0218424 A1 7/2024 Costa et al.
2024/0218437 A1 7/2024 Belhocine et al.
2024/0263219 A1 8/2024 Kuhnemund
2024/0263220 A1 8/2024 Olofsson
2024/0264155 A1 8/2024 Costa
2024/0301475 A1 9/2024 Mielinis
2024/0305314 A1 9/2024 Hoffman et al.
2024/0331348 A1 10/2024 Bava et al.
2024/0351041 A1 10/2024 Christopherson et al.
2024/0368677 A1 11/2024 Mignardi
2024/0368678 A1 11/2024 Bloju
2024/0369471 A1 11/2024 Hoffman et al.
2024/0376521 A1 11/2024 Costa et al.
2024/0384330 A1 11/2024 Mignardi et al.
2024/0428880 A1 12/2024 Marks et al.
2025/0043339 A1 2/2025 Wang et al.
2025/0075263 A1 3/2025 Bent et al.
2025/0075267 A1 3/2025 Hayes et al.
2025/0092443 A1 3/2025 Oh
2025/0129411 A1 4/2025 Sasaki et al.
2025/0163502 A1 5/2025 Costa et al.
2025/0179571 A1 6/2025 Sasaki
2025/0188519 A1 6/2025 Mignardi et al.
2025/0207189 A1 6/2025 Chitnis et al.
2025/0207203 A1 6/2025 Schnall-Levin
2025/0236906 A1 7/2025 Bloju
2025/0257391 A1 8/2025 Mignardi
2025/0257394 A1 8/2025 Chitnis et al.
2025/0263783 A1 8/2025 Sasaki et al.
2025/0270636 A1 8/2025 Bell et al.
2025/0277262 A1 9/2025 Chitnis et al.
2025/0327114 A1 10/2025 Marks et al.

FOREIGN PATENT DOCUMENTS

WO WO-2007048629 A2 5/2007
WO WO-2017075294 A1 5/2017
WO WO 2017/143155 8/2017
WO WO-2018112336 A1 6/2018
WO WO 2019/199579 10/2019
WO WO-2019222036 A1 11/2019
WO WO 2020/076976 4/2020
WO WO 2020/076979 4/2020
WO WO 2020/096687 5/2020
WO WO 2020/099640 5/2020
WO WO 2020/117914 6/2020
WO WO 2020/123316 6/2020
WO WO 2020/123742 6/2020
WO WO 2020/142490 7/2020
WO WO 2020/240025 12/2020
WO WO 2020/254519 12/2020
WO WO 2021/123282 6/2021

(56) References Cited

FOREIGN PATENT DOCUMENTS

| | | |
|---|---|---|
| WO | WO 2021/123286 | 6/2021 |
| WO | WO-2021138676 A1 | 7/2021 |
| WO | WO 2021/155063 | 8/2021 |
| WO | WO 2021/168326 | 8/2021 |
| WO | WO-2022056078 A1 | 3/2022 |
| WO | WO-2022222920 A1 | 10/2022 |
| WO | WO-2023108139 A2 | 6/2023 |
| WO | WO-2023141476 A1 | 7/2023 |
| WO | WO-2023172915 A1 | 9/2023 |
| WO | WO-2023192302 A1 | 10/2023 |
| WO | WO-2024148300 A1 | 7/2024 |

OTHER PUBLICATIONS

Conze et al., "Single molecule analysis of combinatorial splicing," Nucleic Acids Res. (2010) 38(16): e163.
Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.
Femino et al., "Visualization of single RNA transcripts in situ," Science. (1998) 280(5363): 585-90.
Forcucci et al., "All-plastic miniature fluorescence microscope for point-of-care readout of bead-based bioassays," J Biomed Opt. (2015) 20(10): 105010.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Glass et al., "SIMPLE: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Gunderson et al. "Decoding randomly ordered DNA arrays." Genome research 14.5 (2004): 870-877.
Gyllborg et al., "Hybridization-based in situ sequencing (HybISS) for spatially resolved transcriptomics in human and mouse brain tissue," Nucleic Acids Res. (2020) 48(19): e112.
Han et al., "Quantum-dot-tagged microbeads for multiplexed optical coding of biomolecules," Nat Biotechnol. (2001) 19(7): 631-5.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Jamur et al., "Permeabilization of cell membranes," Method Mol. Biol. (2010) 588: 63-66 (abstract only).
Korlach et al. "Selective aluminum passivation for targeted immobilization of single DNA polymerase molecules in zero-mode waveguide nanostructures." *Proceedings of the National Academy of Sciences* 105.4 (2008): 1176-1181.
Krzywkowski et al., "Fidelity of RNA templated end-joining by chlorella virus DNA ligase and a novel iLock assay with improved direct RNA detection accuracy," Nucleic Acids Res. (2017) 45(18): e161.
Lagunavicius et al., "Novel application of Phi29 DNA polymerase: RNA detection and analysis in vitro and in situ by target RNA-primed RCA," RNA. (2009) 15(5):765-71.
Lagunavicius et al., "Duality of polynucleotide substrates for Phi29 DNA polymerase: 3'→5' RNase activity of the enzyme," RNA. (2008) 14(3):503-13.
Lakowicz et al., "Silver particles enhance emission of fluorescent DNA oligomers," Bio Techniques (2003) 34(1); 62-66.
Larsson et al. "In situ detection and genotyping of individual mRNA molecules," Nat Methods. (2010) 7(5):395-397.
Lee et al. "Highly Multiplexed Subcellular RNA Sequencing In Situ", Science (2014) 343(6177):1360-1363.
Levene et al. "Zero-mode waveguides for single-molecule analysis at high concentrations." *science* 299.5607 (2003): 682-686.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Lin et al., "Highly multiplexed imaging of single cells using a high-throughput cyclic immunofluorescence method," Nat Commun. (2015) 6:8390.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Lugunavicius et al., "Novel application of Phi29 DNA polymerase: RNA detection and analysis in vitro and in situ by target RNA-primed RCA," RNA. (2009) 15(5):765-71.
Lundquist et al. "Parallel confocal detection of single molecules in real time." Optics letters 33.9 (2008): 1026-1028.
Lyamichev et al., "Comparison of the 5' nuclease activities of taq DNA polymerase and its isolated nuclease domain," Proc Natl Acad Sci USA. (1999) 96(11): 6143-6148.
Ma et al., "RNA template-dependent 5' nuclease activity of *Thermus aquaticus* and *Thermus thermophilus* DNA polymerases," J Biol Chem. (2000) 275(32): 24693-700.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Rouhanifard et al. "ClampFISH detects individual nucleic acid molecules using click chemistry-based amplification," Nat Biotechnol. (2018) 17 pages. doi: 10.1038/nbt.4286.
Shendure et al, "Accurate multiplex polony sequencing of an evolved bacterial genome," Science (2005) 309(5741); 1728-1732.
Sun et al., "Composite organic-inorganic nanoparticles as Raman labels for tissue analysis," Nano Lett. (2007) 7(2): 351-6.
Takahashi et al., "RNase H-assisted RNA-primed rolling circle amplification for targeted RNA sequence detection," Sci Rep. (2018) 8(1):7770.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Vandernoot et al., "cDNA normalization by hydroxyapatite chromatography to enrich transcriptome diversity in RNA-seq applications," Biotechniques, (2012) 53(6) 373-80.
Wählby et al., "Sequential immunofluorescence staining and image analysis for detection of large numbers of antigens in individual cell nuclei," Cytometry. (2002) 47(1): 32-41.
Wang et al., "Three-dimensional intact-tissue sequencing of single-cell transcriptional states," Science. (2018) 361(6400): eaat5691.

(56) References Cited

OTHER PUBLICATIONS

Weibrecht et al., "Simultaneous visualization of both signaling cascade activity and end-point gene expression in single cells," PLoS One. (2011) 6(5): e20148.
Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu, C. et al. "RollFISh Achieves Robust Quantification of Single-Molecule RNA Biomarkers In Paraffin-Embedded Tumor Tissue Samples," Commun Biol. (2018) 1:(209):1-8. doi: 10.1038/s42003-018-0218-0.
Zhao et al., "Advances of multiplex and high throughput biomolecular detection technologies based on encoding microparticles," Sci China Chem. (2011) 54(8):1185.
Allawi, Hatim T. and John SantaLucia. Thermodynamics and NMR of internal G T mismatches in DNA. Biochemistry 36(34):10581-10594 (1997).
Batra et al., Elimination of Toxic Microsatellite Repeat Expansion RNA by RNA-Targeting Cas9. Cell, 170(50:899-912.e10 (2017).
Chen, Xiaoyin. et al. Efficient in situ barcode sequencing using padlock probe-based BaristaSeq. Nucleic acids research 46(4):e22, 1-10 (2018).
Faruqi, Fawad A. et al. High-throughput genotyping of single nucleotide polymorphisms with rolling circle amplification. BMC genomics 2:4, 1-10 (2001).
Frank, Peter. et al. Purification and characterization of human ribonuclease HII. Nucleic acids research 22(24):5247-5254 (1994).
Gao et al., "Rolling circle amplification integrated with suspension bead array for ultrasensitive multiplex immunodetection of tumor markers," Anal Chim Acta. (2019): 1048:75-84.
Gao, Ruixuan. et al. QandA: Expansion microscopy, BMC Biology 15(1):50, 1-9 (2017).
Garafutdinov et al., "Rolling circle amplification as a Universal Method for the Analysis of a wide range of biological targets'," Russian Journal of Bioorganic Chemistry (2021) 47(6):1172-1189.
Gruber et al., "Vitamin B12-derivatives-enzyme cofactors and ligands of proteins and nucleic acids," Chem Soc Rev. (2011) 40(8):4346-63.
Han et al., "Improving protein solubility and activity by introducing small peptide tags designed with machine learning models," Metab Eng Commun. (2020) 11:e00138.
Henikoff, Steven et al.: Amino Acid Substitution Matrices From Protein Blocks. Proceedings of the National Academy of Sciences of the United States of America 89(22):10915-10919 (1992).
Huynh et al., "A versatile toolkit for CRISPR-Cas13-based RNA manipulation in *Drosophila*," Genome Biol. (2020) 21(1):279.
Hyjek et al., "RNases H: Structure and mechanism," DNA Repair (Amst). (2019) 84:102672.
Iwasaki et al., Defining fundamental steps in the assembly of the *Drosophila* RNAi enzyme complex. Nature, 521(7553):533-536 (2015).
Jamur, Maria Celia, and Constance Oliver. Chapter 9: Permeabilization of cell membranes. Methods in Molecular Biology 588:63-66 (2010).
Ke et al., "SeeDB: a simple and morphology-preserving optical clearing agent for neuronal circuit reconstruction," Nat Neurosci. (2013) 16(8):1154-1161.
Kielpinski et al., "RNase H sequence preferences influence antisense oligonucleotide efficiency," Nucleic Acids Res. (2017) 45(22):12932-12944.
Lamture, J.B. et al. Direct Detection of Nucleic Acid Hybridization on the Surface of a Charge Coupled Device. Nucleic Acids Research 22(11):2121-2125 (1994).
Lei et al., Structure-function analysis of human glucose-6-phosphatase, the enzyme deficient in glycogen storage disease type 1a. J. Biol. Chem. 270(20):11882-118826 (1995).
Li et al., A programmable pAgo nuclease with RNA target preference from the psychrotolerant bacterium *Mucilaginibacter paludis*. Nucleic Acids Res. 50(9):5226-5238.
Lisitskaya et al., "Programmable RNA targeting by bacterial Argonaute nucleases with unconventional guide binding and cleavage specificity," Nat Commun. (2022) 13(1):4624.
Macosko, Evan Z. et al. Highly Parallel Genome-wide Expression Profiling of Individual Cells Using Nanoliter Droplets. Cell 161(5):1202-1214 (2015). With Supplementary Information.
McGeary et al., "The biochemical basis of microRNA targeting efficacy," Science. (2019) 366(6472):eaav1741.
Mota, Ana et al. Simultaneous visualization of DNA loci in single cells by combinatorial multi-color iFISH. Scientific data 9(1):47, 1-15 (2022).
Murakami et al., "Sensitive RNA detection by combining three-way junction formation and primer generation-rolling circle amplification," Nucleic Acids Res. (2012) 40(3):e22.
O'Connell et al., "Programmable RNA recognition and cleavage by CRISPR/Cas9," Nature, 2014; 516: pp. 263-266.
Pavlov et al., "Helix-hairpin-helix motifs confer salt resistance and processivity on chimeric DNA polymerases," Proc Natl Acad Sci USA. (2002) 99(21):13510-5.
Qi, et al., "Fur in Magnetospirillum gryphiswaldense influences magnetosomes formation and directly regulates the genes involved in iron and oxygen metabolism," PLoS One. (2012) 7(1):e29572.
Rogers et al., "Use of a novel cross-linking method to modify adenovirus tropism," Gene Ther. (1997) 4(12): 1387-1392.
Rozi et al., "The mechanism and improvements to the isothermal amplification of nucleic acids, at a glance," Anal Biochem. (2021) 631:114260.
Sternberg, Samuel H. et al. DNA Interrogation by the CRISPR RNA-guided Endonuclease Cas9. Nature 507(7490):62-67 (2014).
Strutt et al., RNA-dependent RNA targeting by CRISPR-Cas9. Elife. Jan. 5, 2018;7:e32724. doi: 10.7554/eLife.32724.
Sugiman-Marangos et al., "Mechanism for accurate, protein-assisted DNA annealing by *Deinococcus radiodurans* DdrB," Proc Natl Acad Sci USA. (2016) 113(16):4308-4313.
Sun et al., An Argonaute from *Thermus parvatiensis* exhibits endonuclease activity mediated by 5' chemically modified DNA guides. Acta Biochim. Biophys. Sin (Shanghai) 54(5):686-695 (2022).
Sun, Yu-Chi. et al. Integrating barcoded neuroanatomy with spatial transcriptional profiling enables identification of gene correlates of projections. Nat Neurosci 24(6):873-885 (2021).
Sylwestrak et al. (2016) Multiplexed intact-tissue transcriptional analysis at cellular resolution. Cell 164:792-804.
Takahashi et al., "RNase H-assisted RNA-primed rolling circle amplification for targeted RNA sequence detection," Sci Rep. (2018) 8(1)1770. Supplementary Information.
Vu et al., "Spatial transcriptomics using combinatorial fluorescence spectral and lifetime encoding, imaging and analysis," Nat Commun. (2022) 13(1):169.
Wang et al., "Mutational analysis defines the 5'-kinase and 3'-phosphatase active sites of T4 polynucleotide kinase," Nucleic Acids Res. (2002) 30(4):1073-80.
Wang et al., "Structure and mechanism of T4 polynucleotide kinase: an RNA repair enzyme," EMBO J. (2002) 21(14):3873-80.
Wang, Xiao. et al. Three-dimensional intact-tissue sequencing of single-cell transcriptional states. Science 361(6400):eaat5691, 1-9 (2018).
Wetmur, J G., DNA Probes: Applications of the Principles of Nucleic Acid Hybridization. Critical Reviews in Biochemistry and Molecular Biology 26(3-4):227-259 (1991).
Wu, et al., Multicolor conjugated polymer dots for biological fluorescence imaging, ACS Nano, Nov. 2008, 2(11):2415-23.
Wu et al., "Properties of cloned and expressed human RNase H1," J Biol Chem. (1999) 274(40):28270-28278.
Xiong, Hai, and Frank Seela. Stepwise "click" chemistry for the template independent construction of a broad variety of cross-linked oligonucleotides: Influence of linker length, position, and linking number on DNA duplex stability. The Journal of Organic Chemistry 76(14):5584-5597 (2011).

(56) References Cited

OTHER PUBLICATIONS

Zhang et al., "Single-base mutational analysis of cancer and genetic diseases using membrane bound modified oligonucleotides," Nucleic Acids Res. (1991) 19(14): 3929-33.

* cited by examiner

RNASE H ASSISTED IN SITU ROLLING CIRCLE AMPLIFICATION

CROSS-REFERENCE TO RELATED APPLICATION

This application claims priority to U.S. Provisional Patent Application No. 63/325,088, filed Mar. 29, 2022, entitled "RNase H assisted in situ rolling circle amplification," which is herein incorporated by reference in its entirety for all purposes.

FIELD

The present disclosure generally relates to methods and compositions for in situ detection of analytes in a sample, such as in situ detection of a region of interest in a target nucleic acid or a reporter oligonucleotide in a cell or a cell or tissue sample.

BACKGROUND

Methods are available for analyzing nucleic acids present in a biological sample, such as a cell or a tissue. Current methods of oligonucleotide probe-based assay methods for in situ analysis may suffer from low sensitivity, specificity, and/or detection efficiency and may require careful and laborious optimization. Thus, improved methods for analyzing nucleic acids present in a biological sample are needed. Provided herein are methods, compositions, and kits that meet such and other needs.

BRIEF SUMMARY

Provided herein are methods of analyzing a biological sample. In some aspects, provided herein are methods of using RNase H to assist in rolling circle amplification (RCA) when using circular or circularizable probes to detect a nucleic acid of interest, in particular RNAs of interest. In one aspect, RNase H assisted RCA-based direct RNA detection can be more sensitive than RCA-based direct RNA detection using an external oligonucleotide primer alone. In some embodiments, RNase H assisted RCA-based direct RNA detection is performed without first reverse transcribing target RNA into cDNA. In some embodiments, the external oligonucleotide primer is a DNA primer. In another aspect, sensitivity, efficiency, and/or specificity of RCA-based direct RNA detection can be further increased by combining RNase H treatment with an external oligonucleotide primer. Since the methods herein can improve RCA sensitivity, the performance variability of RCA based nucleic acid detection methods can be improved across different sample types and gene panels.

In some embodiments, provided herein is a method for analyzing a biological sample, comprising: (a) contacting the biological sample with a circular or circularizable probe, wherein the circular or circularizable probe comprises a hybridization region that hybridizes to a target RNA sequence in a target RNA in the biological sample to form a duplex, (b) contacting the biological sample with a primer oligonucleotide, a ribonuclease H (RNase H), and a polymerase, wherein the primer oligonucleotide hybridizes to the circular or circularizable probe; (c) performing rolling circle amplification (RCA) using the circular probe or a circularized probe formed by circularizing the circularizable probe as template; and (d) detecting one or more products of the RCA, thereby detecting the target RNA or a sequence thereof in the biological sample.

In some embodiments, the method further comprises ligating the circularizable probe to form the circularized probe. In some embodiments, the ligating is performed using the target RNA as a template. In any of the embodiments herein, the ligating can be performed using a splint as a template. In any of the embodiments herein, the primer oligonucleotide can be or comprise the splint. In some embodiments, the splint does not comprise a region configured to hybridize to the target RNA sequence.

In any of the embodiments herein, the ligating can be performed prior to contacting the biological sample with the primer oligonucleotide, the RNase H, and/or the polymerase. In some embodiments, the ligating is performed prior to the RNase H cleaving the target RNA in the duplex at one or more sites in the target RNA sequence.

In some of any of the embodiments herein, the ligating can be performed after contacting the biological sample with the primer oligonucleotide, the RNase H, and/or the polymerase. In some embodiments, the ligating is performed using the primer oligonucleotide as a template.

In any of the embodiments herein, the circular or circularizable probe can comprise deoxyribonucleotide residues. In any of the embodiments herein, the circular or circularizable probe may consist of deoxyribonucleotide residues.

In any of the embodiments herein, the circular or circularizable probe can comprise one or more ribonucleotide residues. In any of the embodiments herein, the circularizable probe can comprise a 3' terminal ribonucleotide residue. In any of the embodiments herein, the circular or circularizable probe can comprise two, three, four, five, six, or more consecutive ribonucleotide residues.

In any of the embodiments herein, the biological sample can be contacted with the primer oligonucleotide, the RNase H, and the polymerase simultaneously.

In some of any of the embodiments herein, the biological sample can be contacted with the primer oligonucleotide prior to being contacted with the RNase H and/or the polymerase.

In some of any of the embodiments herein, the biological sample can be contacted with the RNase H prior to being contacted with the primer oligonucleotide and/or the polymerase. In any of the embodiments herein, the biological sample can be contacted with the primer oligonucleotide and/or the polymerase after washing the biological sample to remove excess RNase H.

In some of any of the embodiments herein, the biological sample can be contacted with the RNase H prior to being contacted with the polymerase.

In some of any of the embodiments herein, the biological sample can be contacted with the RNase H simultaneously with or after being contacted with the polymerase.

In any of the embodiments herein, the polymerase can be a Phi29 DNA polymerase or a Bst DNA polymerase. In any of the embodiments herein, the polymerase may have an exonuclease activity and/or an RNase activity.

In any of the embodiments herein, the RNase can comprise an RNase H1 and/or an RNase H2. In some embodiments, the RNase is RNase H1 and/or an RNase H2.

In any of the embodiments herein, the contacting in step (a), the contacting in step (b), and/or the RCA in step (c) are performed in the presence of an RNase inhibitor. In some embodiments, the RNase inhibitor does not inhibit RNase H. In any of the embodiments herein, the RNase H inhibitor can be RNasin.

In any of the embodiments herein, the contacting with the RNase H can comprises: a first step performed in a first buffer that is free or substantially free of a cofactor for the RNase H. In any of the embodiments herein, the cofactor may comprise $Mg^{2+}$ and/or $Mn^{2+}$, and a second step may be performed in a second buffer comprising the cofactor. In some embodiments, the method further comprises incubating the biological sample with the RNase H in the first buffer, thereby allowing the RNase H to bind the target RNA, the circular or circularizable probe, and/or the duplex; removing excess RNase H from the biological sample; and incubating the biological sample in the second buffer, thereby allowing the RNase H to cleave at one or more sites in the target RNA sequence. In any of the embodiments herein, the removing RNase H step may be performed by one or more washes.

In any of the embodiments herein, the RNase H may cleave cleaves the target RNA at no more than two, no more than three, no more than four, no more than five, no more than six, no more than seven, or no more than eight sites in the target RNA sequence. In any of the embodiments herein, the target RNA sequence may be cleaved at only one site by the RNase H.

In any of the embodiments herein, the one or more RCA products can comprise an RCA product generated by using the primer oligonucleotide as a primer.

In any of the embodiments herein, the target RNA sequence can be cleaved by the RNase H to generate a target RNA fragment. In some embodiments, the one or more RCA products comprise an RCA product generated by using the target RNA fragment as a primer.

In any of the embodiments herein, the RCA can be performed for about 10 minutes, about 30 minutes, about 1 hour, about 2 hours, about 3 hours, about 6 hours, about 12 hours, or more than about 12 hours.

In any of the embodiments herein, the biological sample can be contacted with the RNase H at a concentration of between about $1\times10^{-5}$ U/μL and about $1\times10^{0}$ U/μL. In any of the embodiments herein, the biological sample can be contacted with the RNase H at a concentration of between about $1\times10^{-4}$ U/L and about $1\times10^{-1}$ U/μL. In any of the embodiments herein, the biological sample can be contacted with the RNase H at a concentration of between about $1\times10^{-3}$ U/μL and about $2\times10^{-2}$ U/μL.

In any of the embodiments herein, the circular or circularizable probe can comprise a barcode region. In some embodiments, the barcode region comprises one or more barcode sequences. In any of the embodiments herein, the one or more barcode sequences can correspond to a sequence in the target RNA.

In any of the embodiments herein, the method can further comprise inactivating the RNase H prior to and/or after the RCA.

In any of the embodiments herein, the detecting step can comprise contacting the one or more RCA products with one or more detectable probes that hybridize to the one or more RCA products. In some embodiments, the one or more detectable probes hybridize to multiple copies of a barcode sequence in the one or more RCA products, wherein the barcode sequence in the one or more RCA products is complementary to a barcode sequence in the circular or circularizable probe. In any of the embodiments herein, the detecting step can comprise contacting the one or more RCA products with one or more intermediate probes that hybridize to the one or more RCA products, wherein each intermediate probe comprises a sequence that hybridizes to the one or more RCA products and a sequence that hybridizes to one or more detectable probes. In some embodiments, the one or more intermediate probes hybridize to multiple copies of a barcode sequence in the one or more RCA products, wherein the barcode sequence in the one or more RCA products is complementary to a barcode sequence in the circular or circularizable probe. In some embodiments, the detecting step comprises contacting the one or more RCA products with a plurality of detectable probes and/or a plurality of intermediate probes in sequential cycles.

In any of the embodiments herein, the target RNA can be endogenous or exogenous to the biological sample. In any of the embodiments herein, the target RNA can be an mRNA or a non-coding RNA (ncRNA). In any of the embodiments herein, the mRNA can be a nascent RNA, a pre-mRNA, a primary-transcript RNA, a processed RNA, a capped mRNA, a non-capped mRNA, a polyadenylated mRNA, a non-polyadenylated mRNA, a spliced mRNA, or a non-spliced mRNA. In some embodiments, the ncRNA is a tRNA, tsRNA, rRNA, srRNA, miRNA, siRNA, piRNA, snoRNA, snRNA, exRNA, scaRNA, gRNA, or long ncRNA (lncRNA). In any of the embodiments herein, the lncRNA can be Xist or HOTAIR.

In any of the embodiments herein, the target RNA can be linear or circular.

In any of the embodiments herein, the target RNA can be a viral, bacterial, fungal, plant, mammalian, or synthetic RNA.

In any of the embodiments herein, the target RNA can be immobilized in the biological sample. In any of the embodiments herein, the target RNA can be cross-linked to one or more molecules in the biological sample or a matrix embedding the biological sample. In any of the embodiments herein, the matrix can be a hydrogel and the biological sample can be hydrogel-embedded and cleared.

In any of the embodiments herein, the RCA can be performed in situ in the biological sample or a matrix embedding the biological sample. In any of the embodiments herein, the method can comprise imaging the biological sample to detect the one or more RCA products in situ in the biological sample or a matrix embedding the biological sample.

In any of the embodiments herein, the method can comprise detecting the one or more RCA products using sequential hybridization of detectable probes, sequencing by hybridization, sequencing by ligation, sequencing by synthesis, sequencing by binding, or a combination thereof.

In any of the embodiments herein, the biological sample can comprise cells or cellular components. In any of the embodiments herein, the biological sample can be a tissue section. In any of the embodiments herein, the biological sample can be a formalin-fixed, paraffin-embedded (FFPE) sample, a frozen tissue sample, or a fresh tissue sample. In any of the embodiments herein, the biological sample can be fixed or not fixed. In any of the embodiments herein, the biological sample can be permeabilized.

In some embodiments, provided herein is a method for analyzing a biological sample, comprising: (a) contacting the biological sample with a circularizable probe comprising a hybridization region that hybridizes to a target RNA sequence in a target RNA in the biological sample to form a duplex, (b) ligating the circularizable probe to form a circularized probe; (c) contacting the biological sample with: (i) a primer oligonucleotide that hybridizes to the circularized probe, (ii) a ribonuclease H (RNase H), and (iii) a Phi29 DNA polymerase, (d) performing rolling circle amplification (RCA) using the circularized probe as template; and (e) detecting one or more products of the RCA, thereby detecting the target RNA or a sequence thereof in the biological sample.

In some embodiments, the circularizable probe is ligated to form the circularized probe using the target RNA as template. In some embodiments, the circularizable probe is ligated to form the circularized probe using a splint as template. In some embodiments, the primer oligonucleotide is or comprises the splint.

In some embodiments, the RNase H cleaves the target RNA at one or more sites to generate a target RNA fragment. In some embodiments, the target RNA fragment remains hybridized to the circularized probe and is used as a primer for the Phi29 DNA polymerase to generate an RCA product.

In some embodiments, the primer oligonucleotide is used as a primer for the Phi29 DNA polymerase to generate an RCA product.

In some embodiments, provided herein is a method for analyzing a biological sample, comprising: (a) contacting the biological sample with a circularizable probe comprising a hybridization region that hybridizes to a target RNA sequence in a target RNA in the biological sample to form a duplex, (b) ligating the circularizable probe to form a circularized probe; (c) contacting the biological sample with (i) a primer oligonucleotide that hybridizes to the circularized probe, (ii) a ribonuclease H (RNase H), and (iii) a Phi29 DNA polymerase, wherein the contacting with the RNase H comprises: (i) a first step that is performed in a first buffer that is free or substantially free of a cofactor for the RNase H, and (ii) a second step that is performed in a second buffer comprising the cofactor, (d) performing rolling circle amplification (RCA) using the circularized probe as template; and (e) detecting one or more products of the RCA, thereby detecting the target RNA or a sequence thereof in the biological sample. In any of the embodiments herein, the cofactor can comprise $Mg^{2+}$ and/or $Mn^{2+}$.

In some embodiments, the biological sample is contacted with the RNase Hin the first buffer that is free or substantially free of the cofactor for the RNase H. In some embodiments, the biological sample is washed to remove excess RNase H. In some embodiments, the biological sample is contacted with the primer oligonucleotide and/or the Phi29 DNA polymerase after removing excess RNase H.

In some embodiments, the biological sample is contacted with the primer oligonucleotide and the Phi29 DNA polymerase in the second buffer comprising the cofactor for the RNase H. In some embodiments, the cofactor for the RNase H is $Mg^{2+}$.

In some embodiments, the biological sample is a cell or tissue sample. In some embodiments, the one or more products of the RCA are generated at location(s) in the cell or tissue sample. In some embodiments, the one or more products of the RCA are detected at location(s) in the biological sample immobilized on a solid support.

In some embodiments, the RCA is performed in a buffer comprising a crowding agent. In some embodiments, the crowding agent is selected from the group consisting of poly(ethylene glycol) (PEG), glycerol, Ficoll, and dextran sulfate. In some embodiments, the crowding agent is poly (ethylene glycol) (PEG).

In some embodiments, provided herein is a kit comprising a circular or circularizable probe comprising a hybridization region that hybridizes to a target RNA sequence to form a duplex, a primer oligonucleotide that hybridizes to the circular or circularizable probe, and a ribonuclease H (RNase H) that cleaves the duplex at one or more sites in the target RNA sequence. In some embodiments, the kit further comprises a polymerase capable of rolling circle amplification (RCA) using the circular probe or a circularized probe formed by circularizing the circularizable probe as a template, and using the primer oligonucleotide and/or the cleaved target RNA sequence as an RCA primer. In some embodiments, the circular or circularizable probe consists of DNA residues or is composed primarily of DNA residues, and wherein the primer oligonucleotide consists of DNA residues or is composed primarily of DNA residues. In some embodiments, the kit further comprises a ligase capable of ligation of the circularizable probe using the target RNA sequence as a ligation template. In some embodiments, the kit further comprises oligonucleotide probes capable of directly or indirectly binding to an RCA product of the circular or circularized probe.

BRIEF DESCRIPTION OF THE DRAWINGS

The drawings illustrate certain embodiments of the features and advantages of this disclosure. These embodiments are not intended to limit the scope of the appended claims in any manner.

FIG. 3A shows normalized signal density in in situ detection of Satb2 and Prox1 under different RCA conditions, showing greater sensitivity when using RNase H treatment compared to using an external RCA primer (control primer) without RNase H treatment. FIG. 3B shows a representative image of detection of Prox1 in mouse dentate gyrus under different RCA conditions.

DETAILED DESCRIPTION

Figure 1A:
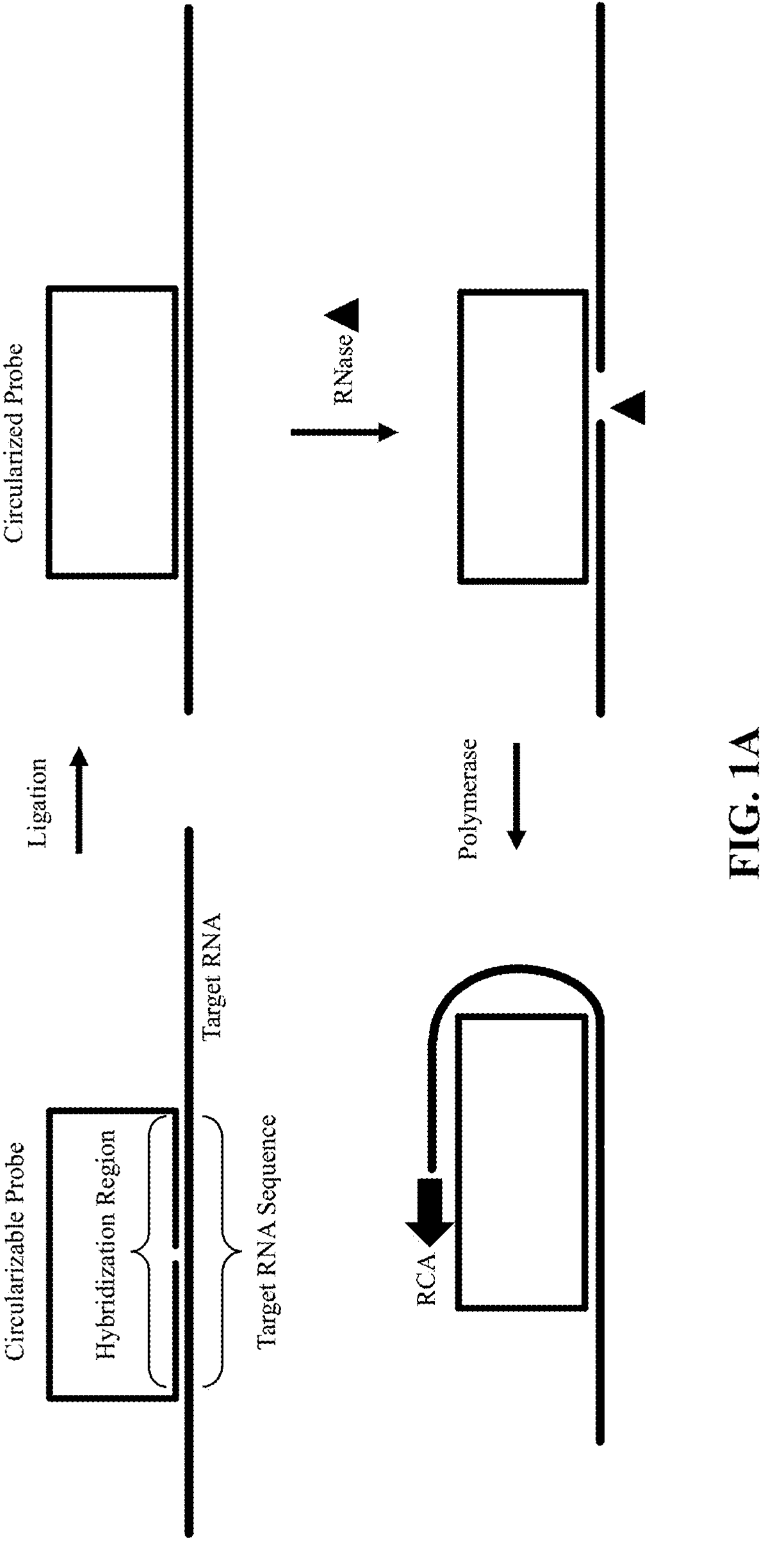
FIG. 1A shows a schematic for an exemplary method of using an RNase to assist in priming an RCA reaction.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

In methods involving rolling circle amplification (RCA), sensitivity of the method depends in part on the initiation efficiency of RCA. In some aspects, RCA sensitivity may be affected by features of the targeted RNA, such as the sequence, secondary structure, or other characteristics of the RNA that affect contacting of the RNA by RCA reagents. In some aspects, the type of tissue sample used for the method may affect the specificity of the RCA.

In some aspects, provided herein are methods for increasing the sensitivity of RCA-based direct RNA detection using RNase (e.g., RNase H) treatment. In some embodiments, the method comprises contacting the biological sample with a circular or circularizable probe, wherein the circular or circularizable probe comprises a hybridization region that hybridizes to a target RNA sequence in a target RNA in the biological sample to form a duplex. In some embodiments, the method further comprises contacting the biological sample with a primer oligonucleotide, a ribonuclease H (RNase H), and a polymerase, in any suitable order, wherein the primer oligonucleotide hybridizes to the circular or circularizable probe. In some embodiments, the method further comprises performing rolling circle amplification (RCA) using the circular probe or a circularized probe formed by circularizing the circularizable probe as template. In some embodiments, the method further comprises detecting one or more products of the RCA, thereby detecting the target RNA or a sequence thereof in the biological sample.

In some aspects, the RNase H assisted RCA increases the efficiency of RCA initiation, thereby increasing the chance that a circular or circularizable probe is amplified during the RCA. In some embodiments, the RNase H assisted RCA leads to greater sensitivity than RCA primed by an external primer oligonucleotide alone. In some embodiments, the RNase H treatment is combined with an external primer oligonucleotide, leading to greater sensitivity than either RNase H treatment or the external primer alone. In some embodiments, the method provides for greater specificity of RCA-based direct RNA detection, e.g., without first converting an RNA target into a cDNA, compared to RCA-based direct RNA detection using external DNA-primed RCA alone or target RNA-primed RCA alone.

II. Samples, Analytes, and Target Sequences

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 μm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 μm. Thicker sections can also be used if desired or convenient, e.g., at least 70, 80, 90, or 100 μm or more. Typically, the thickness of a tissue section is between 1-100 μm, 1-50 μm, 1-30 μm, 1-25 μm, 1-20 μm, 1-15 μm, 1-10 μm, 2-8 μm, 3-7 μm, or 4-6 μm, but as mentioned above, sections with thicknesses larger or smaller than these ranges can also be analyzed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or circularizable (e.g., padlock) probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a circularizable probe (e.g., padlock probe).

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., *Science* 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DIR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Any suitable method of destaining or discoloring a biological sample may be utilized, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNase. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate access of analytes in the sample by probes. If a sample is not permeabilized sufficiently, the quantity of probes that enter the sample and bind to analytes therein may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods can be used. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques,* 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected. In some aspects, the analytes include one of more target nucleic acids. In some embodiments, an analyte can comprise a nucleic acid which hybridizes to a circular probe disclosed herein. In some embodiments, an analyte can comprise an RNA molecule which hybridizes to a circular or circularizable probe disclosed herein. In some embodiments, an analyte can bind to a labelling agent comprising a nucleic acid which hybridizes to a circular probe or circularizable disclosed herein. In some embodiments, an analyte can bind to a labelling agent comprising an RNA molecule which hybridizes to a circular or circularizable probe disclosed herein.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g., an affinity binding partner) can be developed. Such a specific binding partner may be a nucleic acid probe (for a nucleic acid analyte) and may lead directly to the generation of an RCA template (e.g., a padlock or other circularizable probe). Alternatively, the specific binding partner may be coupled to a nucleic acid, which may be detected using an RCA strategy (e.g., in an assay which uses or generates a circular nucleic acid molecule which can be the RCA template).

Analytes of particular interest may include nucleic acid molecules, such as DNA (e.g. genomic DNA, mitochondrial DNA, plastid DNA, viral DNA, etc.) and RNA (e.g., mRNA, microRNA, rRNA, snRNA, viral RNA, etc.), and synthetic and/or modified nucleic acid molecules, (e.g., including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g., including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g., proteins may also be target analytes, for example aggregates of the same protein or different proteins. The analyte may also be a complex between proteins or peptides and nucleic acid molecules such as DNA or RNA, e.g., interactions between proteins and nucleic acids, e.g., regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. In any of the embodiments herein, an analyte binding moiety barcode can be a barcode that is associated with or otherwise identifies the analyte binding moiety. In any of the embodiments herein, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety, e.g., cholesterol) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

C. Target Sequences

A target sequence for a probe disclosed herein may be comprised in any analyte disclose herein, including an endogenous analyte (e.g., a viral or cellular nucleic acid), a labelling agent, or a product of an endogenous analyte and/or a labelling agent. In some embodiments, a target sequence for a probe disclosed herein comprises one or more ribonucleotides.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding embodiments, barcodes (e.g., primary and/or secondary barcode sequences) can be analyzed (e.g., detected or sequenced) using any suitable methods or techniques, including those described herein, such as sequencing by synthesis (SBS), sequencing by binding, sequencing by ligation (SBL), or sequencing by hybridization (SBH). In any of the preceding embodiments, the methods provided herein can include analyzing the barcodes by sequential hybridization and detection with a plurality of labelled probes (e.g., detection oligos). In some embodiments, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding embodiments, the methods provided herein can include analyzing the barcodes by sequential hybridization and detection with a plurality of labelled probes (e.g., detection oligos). In some embodiments, the barcode detection steps can be performed as described in hybridization-based in situ sequencing (HybISS). In some embodiments, probes can be detected and analyzed (e.g., detected or sequenced) as performed in fluorescent in situ sequencing (FISSEQ) or spatially resolved transcript amplicon readout mapping (STARmap). In some embodiments, signals associated with an analyte can be detected as performed in sequential fluorescent in situ hybridization (seqFISH).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises 4N complexity given a sequencing read of N bases, and a much shorter sequencing read may be required for molecular identification compared to non-barcode sequencing methods such as direct sequencing. For example, 1024 molecular species may be identified using a 5-nucleotide barcode sequence (45=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and U.S. Pat. Pub. 20210164039, which are hereby incorporated by reference in their entirety.

III. Nucleic Acid Probes

Disclosed herein in some aspects are nucleic acid probes and/or probe sets (e.g., circular or circularizable probes) that are introduced into a cell or used to otherwise contact a biological sample such as a tissue sample. The probes may comprise any of a variety of entities that can hybridize to a nucleic acid, typically by Watson-Crick base pairing, such as DNA, RNA, LNA, PNA, etc. The nucleic acid probe typically contains a sequence (e.g., hybridization region) that can directly or indirectly bind to at least a portion of a target nucleic acid. The nucleic acid probe may be able to bind to a specific target nucleic acid (e.g., an mRNA, or other nucleic acids as discussed herein). In some embodiments, the nucleic acid probes may be detected using a detectable label, and/or by using secondary nucleic acid probes able to bind to the nucleic acid probes or sequences thereof. In some embodiments, the nucleic acid probes (e.g., primary probes and/or secondary probes) are compatible with one or more biological and/or chemical reactions. For instance, a nucleic acid probe disclosed herein can serve as template or primer for a polymerase, a template or substrate for a ligase, and/or a substrate for a nuclease (e.g., endonuclease or exonuclease for cleavage or digestion).

In some embodiments, more than one type of primary nucleic acid probes may be contacted with a sample, e.g., simultaneously or sequentially in any suitable order, such as in sequential probe hybridization/unhybridization cycles. In some embodiments, the primary probes may comprise circular probes and/or circularizable probes (such as padlock probes). In some embodiments, more than one type of secondary nucleic acid probes may be contacted with a sample, e.g., simultaneously or sequentially in any suitable order, such as in sequential probe hybridization/unhybridization cycles. In some embodiments, the secondary probes may comprise probes that bind to a product (e.g., an RCA product) of a primary probe targeting an analyte. In some embodiments, more than one type of higher order nucleic acid probes may be contacted with a sample, e.g., simultaneously or sequentially in any suitable order, such as in sequential probe hybridization/unhybridization cycles. In some embodiments, more than one type of detectably labeled nucleic acid probes may be contacted with a sample, e.g., simultaneously or sequentially in any suitable order, such as in sequential probe hybridization/unhybridization cycles. In some embodiments, the detectably labeled probes may comprise probes that bind to one or more primary probes, one or more secondary probes, one or more higher order probes, one or more intermediate probes between a primary/second/higher order probes, and/or one or more detectably or non-detectably labeled probes. In some embodiments, at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid probes (e.g., primary, secondary, higher order probes, and/or detectably labeled probes) can be contacted with a sample, e.g., simultaneously or sequentially in any suitable order. Between any of the probe contacting steps disclosed herein, the method may comprise one or more intervening reactions and/or processing steps, such as modifications of a target nucleic acid, modifications of a probe or product thereof (e.g., via hybridization, ligation, extension, amplification, cleavage, digestion, branch migration, primer exchange reaction, click chemistry reaction, crosslinking, attachment of a detectable label, activating photo-reactive moieties, etc.), removal of a probe or product thereof (e.g., cleaving off a portion of a probe and/or unhybridizing the entire probe), signal modifications (e.g., quenching, masking, photo-bleaching, signal enhancement (e.g., via FRET), signal amplification, etc.), signal removal (e.g., cleaving off or permanently inactivating a detectable label), crosslinking, de-crosslinking, and/or signal detection.

The target-binding sequence (e.g., hybridization region) of a probe may be positioned anywhere within the probe. For instance, the target-binding sequence of a primary probe that binds to a target nucleic acid can be 5' or 3' to any barcode sequence in the primary probe. Likewise, the target-binding sequence of a secondary probe (which binds to a primary probe or complement or product thereof) can be 5' or 3' to any barcode sequence in the secondary probe. In some embodiments, the target-binding sequence may comprise a sequence that is substantially complementary to a portion of a target nucleic acid. In some embodiments, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary.

The target-binding sequence of a primary nucleic acid probe may be determined with reference to a target nucleic acid (e.g., a cellular RNA or a reporter oligonucleotide of a labelling agent for a cellular analyte) that is present or suspected of being present in a sample. In some embodiments, more than one target-binding sequence can be used to identify a particular analyte comprising or associated with a target nucleic acid. The more than one target-binding sequence can be in the same probe or in different probes. For instance, multiple probes can be used, sequentially and/or simultaneously, that can bind to (e.g., hybridize to) different regions of the same target nucleic acid. In other examples, a probe may comprise target-binding sequences that can bind to different target nucleic acid sequences, e.g., various intron and/or exon sequences of the same gene (for detecting splice variants, for example), or sequences of different genes, e.g., for detecting a product that comprises the different target nucleic acid sequences, such as a genome rearrangement (e.g., inversion, transposition, translocation, insertion, deletion, duplication, and/or amplification).

In some aspects, a primary probe, a secondary probe, and/or a higher order probe can be selected from the group consisting of a circular probe, a circularizable probe, and a linear probe. In some embodiments, a circular probe can be one that is pre-circularized prior to hybridization to a target nucleic acid and/or one or more other probes. In some embodiments, a circularizable probe can be one that can be circularized upon hybridization to a target nucleic acid and/or one or more other probes such as a splint. In some embodiments, a linear probe can be one that comprises a target recognition sequence and a sequence that does not hybridize to a target nucleic acid, such as a 5' overhang, a 3' overhang, and/or a linker or spacer (which may comprise a nucleic acid sequence or a non-nucleic acid moiety). In some embodiments, the sequence (e.g., the 5' overhang, 3' overhang, and/or linker or spacer) is non-hybridizing to the target nucleic acid but may hybridize to one another and/or one or more other probes, such as detectably labeled probes.

Specific probe designs can vary depending on the application. For instance, a primary probe, a secondary probe, and/or a higher order probe disclosed herein can comprise a circularizable probe or probe set (e.g., padlock probe) that does require gap filling to circularize upon hybridization to a template (e.g., a target nucleic acid and/or a probe such as a splint), a gapped circularizable probe (e.g., one that require gap filling to circularize upon hybridization to a template), an L-shaped probe (e.g., one that comprises a target recognition sequence and a 5' or 3' overhang upon hybridization to a target nucleic acid or a probe), a U-shaped probe (e.g., one that comprises a target recognition sequence, a 5' overhang, and a 3' overhang upon hybridization to a target nucleic acid or a probe), a V-shaped probe (e.g., one that comprises at least two target recognition sequences and a linker or spacer between the target recognition sequences upon hybridization to a target nucleic acid or a probe), a probe or probe set for proximity ligation (such as those described in U.S. Pat. Nos. 7,914,987 and 8,580,504, incorporated herein by reference in their entireties, and probes for Proximity Ligation Assay (PLA) for the simultaneous detection and quantification of nucleic acid molecules and protein-protein interactions), or any suitable combination thereof. In some embodiments, a primary probe, a secondary probe, and/or a higher order probe disclosed herein can comprise a probe that is ligated to itself or another probe using DNA-templated and/or RNA-templated ligation. In some embodiments, a primary probe, a secondary probe, and/or a higher order probe disclosed herein can be a DNA molecule and can comprise one or more other types of nucleotides, modified nucleotides, and/or nucleotide analogues, such as one or more ribonucleotides. In some embodiments, the ligation can be a DNA ligation on a DNA template. In some embodiments, the ligation can be a DNA ligation on an RNA template, and the probes can comprise RNA-templated ligation probes. In some embodiments, a primary probe, a secondary probe, and/or a higher order probe disclosed herein can comprise a circularizable probe or probe set (e.g., padlock probe). In some embodiments, a nucleic acid probe disclosed herein is part of a SNAIL (Splint Nucleotide Assisted Intramolecular Ligation) probe set, such as one described in US 2019/0055594 or US 2021/0164039, which are incorporated herein by reference in their entireties. In some embodiments, a nucleic acid probe disclosed herein is part of a PLAYR (Proximity Ligation Assay for RNA) probe set, such as one described in US 2016/0108458, which is incorporated herein by reference in its entirety. In some embodiments, a nucleic acid probe disclosed herein is part of a PLISH (Proximity Ligation in situ Hybridization) probe set, such as one described in US 2020/0224243, which is incorporated herein by reference in its entirety. Any suitable combination of the probe designs described herein can be used.

In some embodiments, a probe disclosed herein (e.g., a circular or circularizable probe) can comprise a 5' flap which may be recognized by a structure-specific cleavage enzyme, e.g., an enzyme capable of recognizing the junction between single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridized to the target nucleic acid molecule, as well as by the 5' and 3' ends of a one-part probe. Enzymes suitable for such cleavage include Flap endonucleases (FENS), which are a class of enzymes having endonucleolytic activity and being capable of catalyzing the hydrolytic cleavage of the phosphodiester bond at the junction of single- and double-stranded DNA. Thus, in some embodiment, cleavage of the additional sequence 5' to the first target-specific binding site is performed by a structure-specific cleavage enzyme, e.g., a Flap endonuclease. Suitable Flap endonucleases are described in Ma et al. 2000. *JBC* 275, 24693-24700 and in US 2020/0224244 (herein incorporated by reference in their entireties) may include *P. furiosus* (Pfu), *A. fulgidus* (Afu), *M. jannaschii* (Mja) or *M. thermoautotrophicum* (Mth). In other embodiments an enzyme capable of recognizing and degrading a single-stranded oligonucleotide having a free 5' end may be used to cleave an additional sequence (5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g., dinucleotides or trinucleotides), or cleaving the entire 5' single-stranded region, e.g., as described in Lyamichev et al. 1999. *PNAS* 96, 6143-6148 for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

Any suitable circularizable probe or probe set, or indeed more generally circularizable reporter molecules, may be used to generate the RCA template which is used to generate the RCA product. In some embodiments, a "circularizable probe is in the form of a linear molecule having ligatable ends which may be circularized by ligating the ends together directly or indirectly, e.g., to each other, or to the respective ends of an intervening ("gap") oligonucleotide or to an extended 3' end of the circularizable probe. A circularizable probe may also be provided in two or more parts, namely two or more molecules (e.g., oligonucleotides) which may be ligated together to form a circle. When said RCA template is circularizable it is circularized by ligation prior to RCA. Ligation may be templated using a ligation template, and in the case of padlock and molecular inversion probes and such like the target analyte may provide the ligation template, or it may be separately provided. The circularizable RCA template (or template part or portion) will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

In the case of padlock probes, in one embodiment the ends of the padlock probe may be brought into proximity to each other by hybridization to adjacent sequences on a target nucleic acid molecule (such as a target analyte), which acts as a ligation template, thus allowing the ends to be ligated together to form a circular nucleic acid molecule, allowing the circularized padlock probe to act as template for an RCA reaction. In such an example the terminal sequences of the padlock probe which hybridize to the target nucleic acid molecule will be specific to the target analyte in question, and will be replicated repeatedly in the RCA product. They may therefore act as a marker sequence indicative of that target analyte. Accordingly, it can be seen that the marker sequence in the RCA product may be equivalent to a sequence present in the target analyte itself. Alternatively, a marker sequence (e.g., tag or barcode sequence) may be provided in the non-target complementary parts of the padlock probe. In still a further embodiment, the marker sequence may be present in the gap oligonucleotide which is hybridized between the respective hybridized ends of the padlock probe, where they are hybridized to non-adjacent sequences in the target molecule. Such gap-filling padlock probes are akin to molecular inversion probes.

In some embodiments, similar circular RCA template molecules can be generated using molecular inversion probes. Like padlock probes, these are also typically linear nucleic acid molecules capable of hybridizing to a target nucleic acid molecule (such as a target analyte) and being circularized. The two ends of the molecular inversion probe may hybridize to the target nucleic acid molecule at sites which are proximate but not directly adjacent to each other, resulting in a gap between the two ends. The size of this gap may range from only a single nucleotide in some embodiments, to larger gaps of 100 to 500 nucleotides, or longer, in other embodiments. Accordingly, it is necessary to supply a polymerase and a source of nucleotides, or an additional gap-filling oligonucleotide, in order to fill the gap between the two ends of the molecular inversion probe, such that it can be circularized.

As with the padlock probe, the terminal sequences of the molecular inversion probe which hybridize to the target nucleic acid molecule, and the sequence between them, will be specific to the target analyte in question, and will be replicated repeatedly in the RCA product. They may therefore act as a marker sequence indicative of that target analyte. Alternatively, a marker sequence (e.g., tag or barcode sequence) may be provided in the non-target complementary parts of the molecular inversion probe.

In some embodiments, the probes disclosed herein may be invader probes, e.g., for generating a circular nucleic acid such as a circularized probe. Such probes are of particular utility in the detection of single nucleotide polymorphisms. The detection method of the present disclosure may, therefore, be used in the detection of a single nucleotide polymorphism, or indeed any variant base, in the target nucleic acid sequence. Probes for use in such a method may be designed such that the 3' ligatable end of the probe is complementary to and capable of hybridizing to the nucleotide in the target molecule which is of interest (the variant nucleotide), and the nucleotide at the 3' end of the 5' additional sequence at the 5' end of the probe or at the 5' end of another, different, probe part is complementary to the same said nucleotide, but is prevented from hybridizing thereto by a 3' ligatable end (e.g., it is a displaced nucleotide). Cleavage of the probe to remove the additional sequence provides a 5' ligatable end, which may be ligated to the 3' ligatable end of the probe or probe part if the 3' ligatable end is hybridized correctly to (e.g. is complementary to) the target nucleic acid molecule. Probes designed according to this principle provide a high degree of discrimination between different variants at the position of interest, as only probes in which the 3' ligatable end is complementary to the nucleotide at the position of interest may participate in a ligation reaction. In one embodiment, the probe is provided in a single part, and the 3' and 5' ligatable ends are provided by the same probe. In some embodiments, an invader probe is a padlock probe (an invader padlock or "iLock"), e.g., as described in Krzywkowski et al., *Nucleic Acids Research* 45, e161, 2017, and US 2020/0224244, which are incorporated herein by reference in their entirety.

Other types of probe which result in circular molecules which can be detected by RCA and which comprise either a target analyte sequence or a complement thereof include selector-type probes described in US 2019/0144940 (herein incorporated by reference in its entirety), which comprise sequences capable of directing the cleavage of a target nucleic acid molecule (e.g. a target analyte) so as to release a fragment comprising a target sequence from the target analyte and sequences capable of templating the circularization and ligation of the fragment. US 2018/0327818, the content of which is herein incorporated by reference in its entirety, describes probes which comprise a 3' sequence capable of hybridizing to a target nucleic acid molecule (e.g. a target analyte) and acting as a primer for the production of a complement of a target sequence within the target nucleic acid molecule (e.g. by target templated extension of the primer), and an internal sequence capable of templating the circularization and ligation of the extended probe comprising the reverse complement of the target sequence within the target analyte and a portion of the probe. In the case of both such probes, target sequences or complements thereof are incorporated into a circularized molecule which acts as the template for the RCA reaction to generate the RCA product, which consequently comprises concatenated repeats of said target sequence. In some embodiments, said target sequence may act as, or may comprise a marker sequence within the RCA product indicative of the target analyte in question. Alternatively, a marker sequence (e.g., tag or barcode sequence) may be provided in the non-target complementary parts of the probes.

In some embodiments, a nucleic acid probe disclosed herein can be pre-assembled from multiple components, e.g., prior to contacting the nucleic acid probe with a target nucleic acid or a sample. In some embodiments, a nucleic acid probe disclosed herein can be assembled during and/or after contacting a target nucleic acid or a sample with multiple components. In some embodiments, a nucleic acid probe disclosed herein is assembled in situ in a sample. In some embodiments, the multiple components can be contacted with a target nucleic acid or a sample in any suitable order and any suitable combination. For instance, a first component and a second component can be contacted with a target nucleic acid, to allow binding between the components and/or binding between the first and/or second components with the target nucleic acid. Optionally a reaction involving either or both components and/or the target nucleic acid, between the components, and/or between either one or both components and the target nucleic acid can be performed, such as hybridization, ligation, primer extension and/or amplification, chemical or enzymatic cleavage, click chemistry, or any combination thereof. In some embodiments, a third component can be added prior to, during, or after the reaction. In some embodiments, a third component can be added prior to, during, or after contacting the sample with the first and/or second components. In some embodiments, the first, second, and third components can be contacted with the sample in any suitable combination, sequentially or simultaneously. In some embodiments, the nucleic acid probe can be assembled in situ in a stepwise manner, each step with the addition of one or more components, or in a dynamic process where all components are assembled together. One or more removing steps, e.g., by washing the sample such as under stringent conditions, may be performed at any point during the assembling process to remove or destabilize undesired intermediates and/or components at that point and increase the chance of accurate probe assembly and specific target binding of the assembled probe.

IV. RNase H Assisted RCA

Provided herein are methods for increasing the sensitivity of RCA-based direct RNA detection in an assay using RNase (e.g., RNase H) treatment. In some embodiments, the method comprises contacting the biological sample with a circular or circularizable probe (e.g., as described in Section III), wherein the circular or circularizable probe comprises a hybridization region that hybridizes to a target RNA sequence in a target RNA in the biological sample to form a duplex. In some embodiments, the method further comprises contacting the biological sample with a primer oligonucleotide, a ribonuclease H (RNase H), and a polymerase, in any suitable order, wherein the primer oligonucleotide hybridizes to the circular or circularizable probe. In some embodiments, the method further comprises performing rolling circle amplification (RCA) using the circular probe or a circularized probe formed by circularizing the circularizable probe as template and detecting one or more products of the RCA, thereby detecting the target RNA or a sequence thereof in the biological sample.

A. Ligation

In some instances, the circular or circularizable probe is hybridized to the target nucleic acid (e.g., target RNA) and ligated to form a circular template for RCA. In some embodiments, provided herein is a probe or probe set capable of RNA-templated ligation. In some embodiments, the ligation involves chemical ligation. In some embodiments, the ligation involves template dependent ligation. In some embodiments, the ligation involves template independent ligation. In some embodiments, the ligation involves enzymatic ligation. In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase or derivative thereof. In some embodiments, the ligase is a T4 RNA ligase 2 (Rnl2) or derivative thereof. In some embodiments, the ligase is a splintR ligase. In some embodiments, the ligase is a *Chlorella* virus DNA Ligase (PBCV-1 DNA ligase) or derivative thereof, in some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo) nucleotide(s) which are complementary to a splint, a circularizable probe or probe set (e.g., padlock probe), or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo) nucleotide, such that the gap (oligo) nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high-fidelity ligase, such as a thermostable DNA ligase (e.g., a Taq DNA ligase), is used, for example, for ligating two or more probes to form a circular probe disclosed herein. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

B. Rolling Circle Amplification (RCA)

RNase H assisted RCA may provide a number of advantages. For instance, RNase H assisted RCA may provide greater sensitivity in RCA assays than using an external primer oligonucleotide alone. In some aspects, RNase H assisted RCA combined with an external primer oligonucleotide may provide greater sensitivity in an RCA assay than either RNase H or a primer oligonucleotide alone. In some aspects, RNase H assisted RCA may provide greater specificity. In some cases, RNase H assisted RCA does not increase off target RCA product generation. For example, specificity can be determined by using one or more negative control circularizable (e.g., padlock) probes that, if hybridized to a target sequence, may be ligated and produce an RCA product. However, the negative control circularizable probes are known to not bind any target RNA in a sample, and signals associated with RCA products of the negative control probes detected in the sample can be used to determine the specificity of RNase H assisted RCA and off target RCA product generation due to RNase H treatment. In some embodiments, the negative control probes are synthetic oligonucleotides that are not complementary to any cellular nucleic acid (e.g., DNA or RNA) sequences in the sample.

Provided herein are methods for analyzing a biological sample comprising contacting the biological sample with a probe comprising a hybridization region that hybridizes to a target RNA sequence in a target RNA in the biological sample to form a duplex, contacting the biological sample with a primer oligonucleotide, RNase H, and a polymerase, performing RCA using the probe as template, and detecting the RCA products, thereby detecting the target RNA or a sequence thereof in the biological sample. In some embodiments, any of the aforementioned steps except for the detecting step are performed in the presence of an RNase inhibitor. In some embodiments, the RCA is performed in the presence of an RNase inhibitor, such that the target RNA (cleaved by RNase H) can be used as a primer for the RCA and is not cleaved or degraded by other RNases. In some embodiments, the RNase inhibitor does not inhibit RNase H. In some embodiments, the detection of the RCA product is performed in the absence of an RNase inhibitor. In some embodiments, the probe is ligated to form a circular probe. In some embodiments, the primer oligonucleotide hybridizes to the circular probe. In some embodiments, the primer oligonucleotide hybridizes to a backbone region of the circular probe which is outside of the hybridization region of the circular probe that hybridizes to the target RNA sequence. In some embodiments, the primer oligonucleotide hybridizes to a barcode region in the circular probe. In some embodiments, the primer oligonucleotide hybridizes to a contiguous barcode region in the circular probe. In some embodiments, the primer oligonucleotide hybridizes to a noncontiguous barcode region in the circular probe. In some embodiments, the primer oligonucleotide hybridizes to a split barcode region in the circular probe. In some embodiments, the primer oligonucleotide hybridizes to a common region in the circular probe, which common region is shared by two or more circular probes that each targets a different target RNA sequence (e.g., transcripts of different genes).

In some aspects, the RNase H targets the circular or circularizable probe bound to DNA and thus cleaves the target RNA in the duplex at one or more sites in the target RNA sequence to generate a target RNA fragment. In some aspects, the target RNA fragment is used as a primer for performing rolling circle amplification (RCA).

In some aspects, the provided method comprises ligating the circularizable probe to form a circular probe (e.g., as described in Section IV.A). In some embodiments, ligating the circularizable probe is performed prior to contacting the biological sample with a primer oligonucleotide, an RNase H, and/or a polymerase. In some embodiments, ligating the circularizable probe is performed after contacting the biological sample with the primer oligonucleotide, the RNase H, and/or polymerase. In some embodiments, ligating the circularizable probe is performed simultaneously with contacting the biological sample with the primer oligonucleotide, the RNase H, and/or polymerase.

In some embodiments, the biological sample is simultaneously contacted with the primer oligonucleotide, the RNase H, and the polymerase. In some embodiments, the biological sample is contacted with the primer oligonucleotide prior to being contacted with the RNase H and/or the polymerase. In some embodiments, the biological sample is first contacted with the primer oligonucleotide, then contacted with the RNase H, and finally by the polymerase. In some embodiments, the biological sample is first contacted with the RNase H, then contacted with the primer oligonucleotide, and finally by the polymerase. In some embodiments, the biological sample is contacted with the primer oligonucleotide prior to, during, or after the ligating of the circularizable probe to form the circularized probe.

In some embodiments, the biological sample is contacted simultaneously with the RNase H and the polymerase. In some embodiments, the biological sample is contacted with the RNase H prior to being contacted with the polymerase.

In some embodiments, the biological sample is contacted with RNase H prior to being contacted with the polymerase (e.g., Phi29 for RCA) and/or the primer oligonucleotide (e.g., an external primer for RCA). In some embodiments, the biological sample is contacted with RNase H, and then simultaneously contacted with the primer oligonucleotide and the polymerase. In some embodiments, the biological sample is contacted with RNase H in a first buffer that only allows RNase H to bind to its substrate but not to activate its enzyme activity. In some embodiments, the first buffer comprises Tris-Cl, KCl, and a redox reagent such as DTT. In some embodiments, the first buffer is free or substantially free of a cofactor for the RNase H. In some embodiments, the biological sample is incubated in the first buffer for about 5 minutes, about 10 minutes, about 15 minutes, about 30 minutes, about 45 minutes, about 1 hour, about 2 hours, or longer, prior to being contacted with the polymerase and/or the primer oligonucleotide. In some embodiments, the biological sample is incubated in the first buffer at between about 1° C. and about 20° C., such as about 2° C. and about 16° C. or at about 4° C. In some embodiments, after incubation in the first buffer without the cofactor, the biological sample is washed one or more times with a wash buffer (e.g., comprising PBS and a surfactant such as Tween®). In some embodiments, after washing the biological sample, the polymerase and the primer oligonucleotide are added to the biological sample with a second buffer. In some embodiments, the second buffer allows activation of the RNase H nicking activity and simultaneously allows the polymerase to start amplify circular templates. In some embodiments, the second buffer comprises Tris-Cl, a cofactor such as $Mg^{2+}$, ammonium sulfate dNTP, and a redox reagent such as DTT. In some embodiments, the biological sample is incubated in the second buffer for about 5 minutes, about 10 minutes, about 15 minutes, about 30 minutes, about 45 minutes, about 1 hour, about 2 hours, about 3 hours, about 6 hours, or longer, for the polymerase to amplify circular templates in the biological sample. In some embodiments, the biological sample is incubated in the second buffer at between about 4° C. and about 65° C., such as between about 16° C. and about 55° C., between about 30° C. and about 50° C., or between about 35° C. and about 45° C.

In some aspects, the provided methods comprise contacting the biological sample with RNase H at a concentration of about at least $1\times10^{-5}$, $1\times10^{-4}$, $1\times10^{-3}$, $1\times10^{-2}$, $1\times10^{-1}$, 1 U/μL, or higher. In some embodiments, the RNase H concentration is less than 1, $1\times10^{-1}$, $1\times10^{-2}$, $1\times10^{-3}$, $1\times10^{-4}$, $1\times10^{-5}$ U/μL, or less. In some embodiments, the RNase H concentration is between about $1\times10^{-5}$ and about $1\times10^{-4}$, between about $1\times10^{-4}$ and about $1\times10^{-3}$, between about $1\times10^{-3}$ and about $1\times10^{-2}$, between about $1\times10^{-2}$ and about $1\times10^{-1}$, between about $1\times10^{-1}$ and about 1, between about $1\times10^{-5}$ and about $1\times10^{-3}$, between about $1\times10^{-4}$ and about $1\times10^{-2}$, between about $1\times10^{-3}$ and about $1\times10^{-1}$ U/μL, or between about $1\times10^{-2}$ and about 1 U/μL. In some embodiments, the RNase H concentration is about $1\times10^{-4}$, $3\times10^{-4}$, $1\times10^{-3}$, $3\times10^{-3}$, $1\times10^{-2}$, $3\times10^{-2}$, or $1\times10^{-1}$ U/μL.

In some embodiments, the RNase H is RNase H1. In some embodiments, the RNase H is an endoribonuclease that specifically hydrolyzes the phosphodiester bonds of RNA which is hybridized to DNA. In some embodiments, the RNase H does not digest single or double-stranded DNA. In some embodiments, the RNase H requires at least four contiguous bases of RNA for digestion of the RNA hybridized to DNA. In some embodiments, the RNase H does not digest a di-ribonucleotide-containing DNA sequence (e.g., one that is DNA-annealed). In some embodiments, the RNase H does not digest a mono-ribonucleotide-containing DNA sequence (e.g., one that is DNA-annealed). In some embodiments, the RNase H digests a target RNA but does not digest a circular or circularizable probe (e.g., a DNA probe or a probe comprising one or more RNA bases on a DNA backbone) hybridized to the target RNA, such that the digested target RNA can function as an RCA primer using the circular or circularized probe (generated from the circularizable probe) as an RCA template.

In some embodiments, the RNase H is RNase H2. In some embodiments, the RNase H is an endoribonuclease that preferentially nicks 5' to one or more ribonucleotides (e.g., a single ribonucleotide, a diribonucleotide sequence, etc.) within the context of a DNA duplex, leaving 5' phosphate and 3' hydroxyl ends. In some embodiments, the RNase H nicks at multiple sites along an RNA portion hybridized to a DNA. In some embodiments, the RNase H digests a DNA-annealed di-ribonucleotide-containing DNA sequence, whereas the RNA-annealed di-ribonucleotide-containing DNA sequence is not digested. In some embodiments, the RNase H digests a DNA-annealed mono-ribonucleotide-containing DNA sequence, whereas RNA-annealed mono-ribonucleotide-containing DNA sequence is not digested. In some embodiments, the RNase H digests a target RNA but does not digest a circular or circularizable probe (e.g., a DNA probe or a probe comprising one or more RNA bases on a DNA backbone) hybridized to the target RNA, such that the digested target RNA can function as an RCA primer using the circular or circularized probe (generated from the circularizable probe) as an RCA template.

In any of the preceding embodiments, the rolling circle amplification may be performed in a buffer comprising a crowding agent. In some embodiments, the crowding agent is selected from the group consisting of poly(ethylene glycol) (PEG), glycerol, Ficoll®, and dextran sulfate. In any of the preceding embodiments, the crowding agent can be poly(ethylene glycol) (PEG). In any of the preceding embodiments, the PEG can be selected from the group consisting of PEG200, PEG8000, and PEG35000. In any of the preceding embodiments, the buffer may comprise between about 5% and about 15% PEG, optionally wherein the buffer comprises about 10% PEG. In any of the preceding embodiments, the rolling circle amplification may be performed in a buffer comprising PEG (e.g., from about PEG 2K to about PEG 16K). In some embodiments, the PEG is PEG 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v). In some aspects, the crowding agent can be used to stabilize the nucleic acid probes (e.g., circular or circularizable probes) and/or amplification product in a location in the biological sample.

In some embodiments, the analytes, probes and/or amplification product (e.g., rolling circle amplification product) can be anchored to a polymer matrix (e.g., as described in Section II). For example, the polymer matrix can be a hydrogel. In some embodiments, the nucleic acid probe(s) and/or amplification product generated can be modified to contain functional groups that can be used as an anchoring site to attach to a polymer matrix. In some embodiments, a modified probe comprising oligo dT may be used to bind to mRNA molecules of interest, followed by reversible or irreversible crosslinking of the modified probe to the matrix. In some embodiments, cross-linking of the matrix or components to be anchored to the matrix can be performed chemically and/or photochemically, or alternatively by any other suitable hydrogel-formation method.

FIG. 1A shows a schematic for an exemplary method of using an RNase to assist in priming an RCA reaction. A circular or circularizable probe is hybridized to a target RNA in a sample. In methods using a circularizable probe, the probe is circularized using the target RNA as template. The sample is contacted with the RNase (e.g., RNase H), creating one or more nicks in the target RNA. A polymerase (e.g., Phi29) can initiate RCA using a target RNA fragment hybridized to the circular or circularized probe as a primer.

Figure 1B:
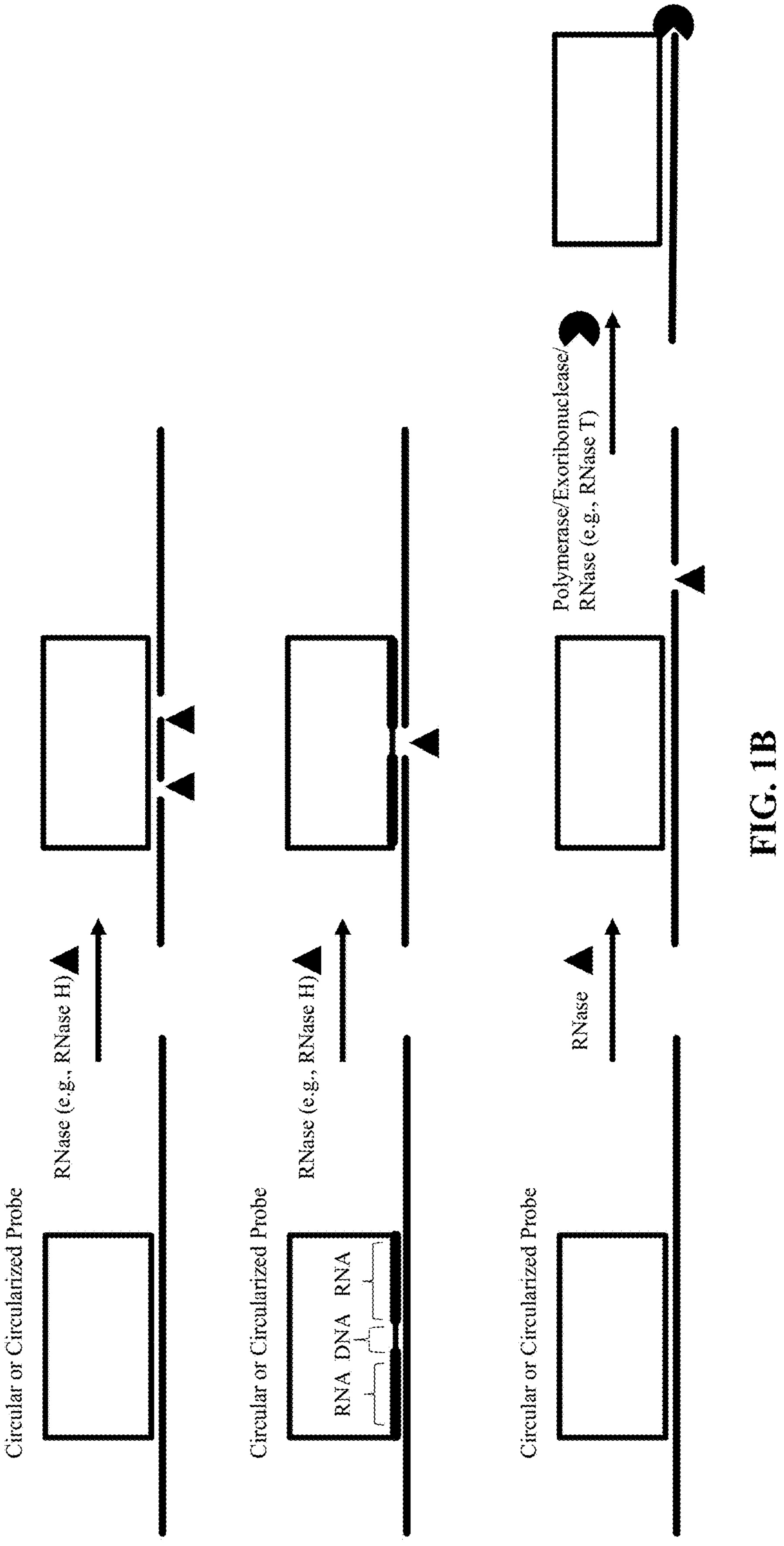
FIG. 1B shows exemplary methods comprising RNase treatment of a sample.

FIG. 1B shows exemplary methods comprising RNase treatment of a sample. In the upper panel of FIG. 1B, the hybridization region of the circular or circularized probe is DNA, and the RNase (e.g., RNase H) cleaves the DNA-annealed target RNA sequence at one or multiple sites. One or more of the target RNA fragments generated by RNase cleavage can be used to prime an RCA reaction using the circular or circularized probe as template.

In some embodiments, the circular or circularizable probe comprises one or more ribonucleotide residues. In some embodiments, the duplex formed between the hybridization region (of the circular or circularizable probe) and the target RNA sequence can comprise DNA-annealed RNA and RNA-annealed RNA. In the middle panel of FIG. 1B, the hybridization region of the circular or circularized probe can comprise RNA sequence(s) and DNA sequence(s), and the RNase (e.g., RNase H) cleaves the DNA-annealed target RNA sequence at one or multiple sites, but not the RNA-annealed target RNA sequence. The hybridization region of the circular or circularized probe can comprise one or multiple DNA sequences flanked by RNA sequences, such that the number of RNase H cleavage sites in the target RNA sequence can be controlled. In some embodiments, the DNA-annealed target RNA sequence is about 2, 3, 4, 5, 6, 7, 8, 9, 10, or more ribonucleotides in length.

In the lower panel of FIG. 1B, the RNase cleaves the target RNA at a site outside the target RNA sequence, creating an overhang that is not hybridized to the circular or circularized probe. An enzyme (e.g., a polymerase such as Phi29, an exoribonuclease, or an RNase, such as RNase T) can be used to chew away the overhang in order for the RNA target to prime RCA. See, e.g., Lagunavicius et al., Duality of polynucleotide substrates for Phi29 DNA polymerase: 3'→5' RNase activity of the enzyme, RNA 2008; 14(3): 503-513, incorporated herein by reference. In some embodiments, the enzyme used to chew away the overhang is a single-stranded RNA specific nuclease. In some embodiments, the enzyme requires a free 3' terminus and removes nucleotides in the 3'→5' direction.

In some embodiments, contacting the biological sample with the RNase H comprises a first step performed in a first buffer that is free or substantially free of a cofactor for the RNase H. In some embodiments, the first buffer comprises a cofactor concentration no more than 10 mM, 9 mM, 8 mM, 7 mM, 6 mM, 5 mM, 4 mM, 3 mM, 2.5 mM, 2 mM, 1.5 mM, 1 mM, 0.5 mM, 0.4 mM, 0.3 mM, 0.2 mM, 0.1 mM, 0.01 mM or less. In some embodiments, the cofactor concentration is between 0 and 0.01 mM, between 0 and 0.1 mM, between 0.1 and 0.5 mM, between 0.5 and 1 mM, between 1 and 1.5 mM, between 1.5 and 2 mM, between 2 and 2.5 mM, between 2.5 and 3 mM, between 3 and 4 mM, between 4 and 5 mM, between 5 and 6 mM, between 6 and 7 mM, between 7 and 8 mM, between 8 and 9 mM, between 9 and 10 mM, between 0 and 1 mM, between 1 and 3 mM, between 3 and 5 mM, or between 5 and 10 mM. In some embodiments, the cofactor comprises a divalent cation. In some embodiments, the divalent cation is magnesium or manganese. In some embodiments, the divalent cation is magnesium. In some embodiments, the first step is prior to or simultaneous with the contacting with the polymerase.

In some embodiments, contacting the biological sample with the RNase H comprises a second step performed in a second buffer containing a cofactor for the RNase H. In some embodiments, the second buffer comprises a cofactor concentration of at least 0.1 mM, 0.2 mM, 0.3 mM, 0.4 mM, 0.5 mM, 1 mM, 1.5 mM, 2 mM, 2.5 mM, 3 mM, 4 mM, 5 mM, 6 mM, 7 mM, 8 mM, 9 mM, 10 mM, 11 mM, 12 mM, 13 mM, 14 mM, 15 mM, or more. In some embodiments, the cofactor concentration is between 0 and 1 mM, between 1 and 2 mM, between 2 and 3 mM, between 3 and 4 mM, between 4 and 5 mM, between 5 and 6 mM, between 6 and 7 mM, between 7 and 8 mM, between 8 and 9 mM, between 9 and 10 mM, between 10 and 15 mM, between 15 and 20 mM, between 20 and 25 mM, between 25 and 30 mM, between 30 and 35 mM, or between 35 and 40 mM. In some embodiments, the cofactor comprises a divalent cation. In some embodiments, the divalent cation is magnesium or manganese. In some embodiments, the divalent cation is magnesium. In some embodiments, the second step is performed subsequent to the first step. In some embodiments, the second step is prior to or simultaneous with the contacting with the polymerase. In some embodiments, RNase H is provided to the sample in a buffer that only allows RNase H to bind to the template but does not activate its activity (e.g., an "OFF" buffer). In some cases, after RNase H binding and washing of excess/non-bound RNase H, the RNase H nicking activity can be activated by providing a different buffer (e.g., an "ON" buffer). In some instances, the "ON" buffer also allows RCA.

In some embodiments, the RNase H requires $Mg^{2+}$ for optimal activity and $Mg^{2+}$ can be at least partially replaced by $Mn^{2+}$. In some embodiments, the RNase H has its maximal activity in the presence of one or more SH-reagents (e.g., dithiothreitol (DTT)) and can be inhibited by reagents such as N-ethylmaleimide.

Figure 1C:
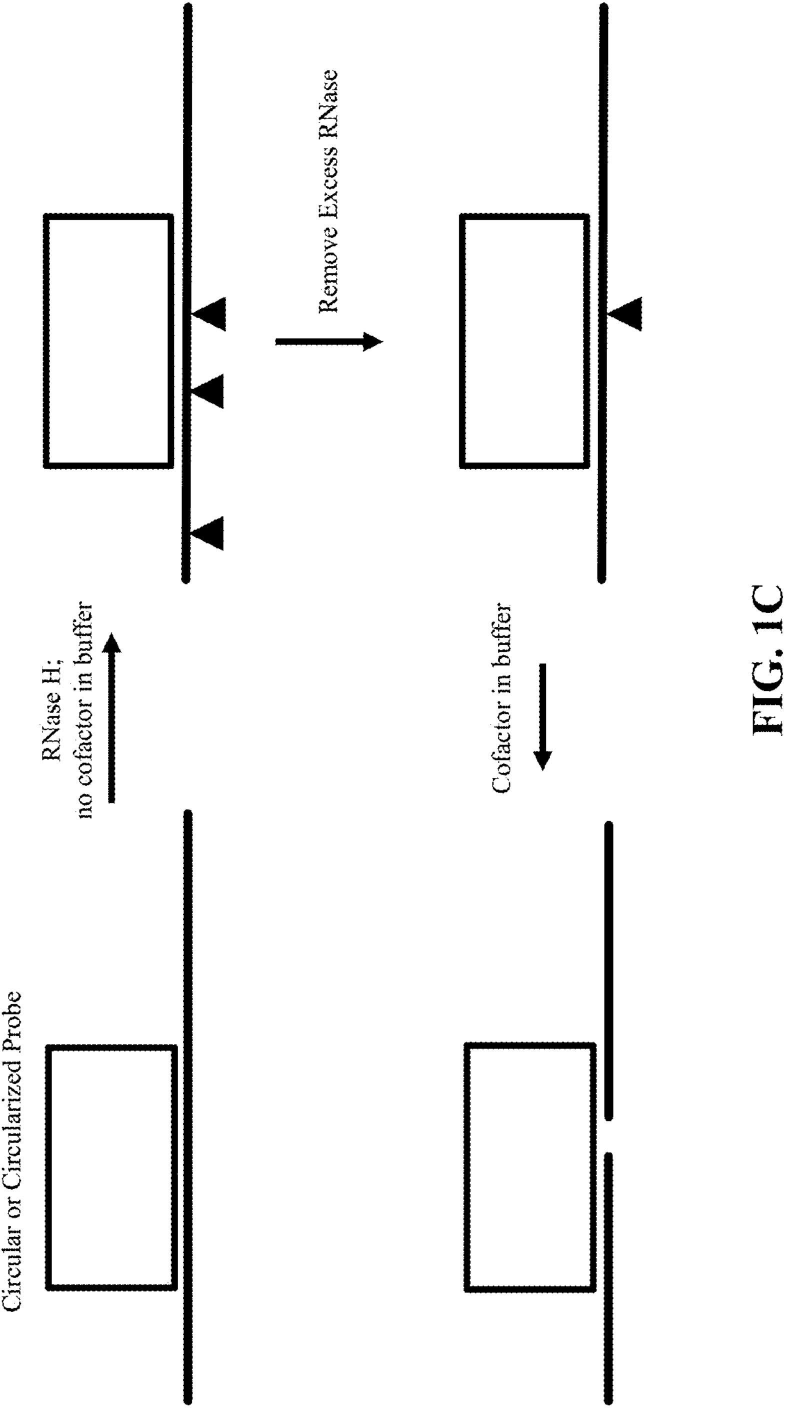
FIG. 1C shows an exemplary method comprising incubating a sample in a first buffer that is free or substantially free of a cofactor, allowing RNase to load, removing excess RNase, and then incubating the sample in a second buffer comprising the cofactor.

FIG. 1C shows an exemplary method comprising incubating a sample in a first buffer that is free or substantially free of a cofactor (e.g., a catalytic cation, such as $Mg^{2+}$ and/or $Mn^{2+}$) for the RNase H (e.g., an "OFF" buffer). In some embodiments, the first buffer may comprise a non-catalytic cation, such as $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, the first buffer comprises $Ca^{2+}$. Molecules of the RNase H can be loaded onto the target RNA and/or circular or circularized probe but do not cleave in the absence of the cofactor. Excess RNase can be removed, for instance, by washing the sample. The sample can be incubated in a second buffer comprising the cofactor (e.g., an "ON" buffer), thereby allowing the loaded RNase H molecules to cleave the DNA-annealed target RNA sequence. In some embodiments, a catalytic cation in the second buffer can replace a non-catalytic cation in complex with the RNase H that is bound to the target RNA, thus turning on the RNase H activity and allowing the enzyme to cleave the DNA-annealed target RNA sequence. In some embodiments, the method further comprises contacting the biological sample with a primer oligonucleotide and a polymerase (e.g., Phi29), wherein the primer oligonucleotide hybridizes to the circular or circularizable probe. RCA can be performed using the circular probe or a circularized probe formed by circularizing the circularizable probe as a template, and using the primer oligonucleotide as well as the RNase H-cleaved target RNA as RCA primers.

In some embodiments, a method disclosed herein comprises contacting a biological sample with a circular or circularizable probe, wherein the circular or circularizable probe comprises a hybridization region that hybridizes to a target RNA sequence in a target RNA in the biological sample to form a duplex; and contacting the biological sample with a primer oligonucleotide, a ribonuclease H (RNase H), and a polymerase (e.g., Phi29) in a first buffer, wherein the primer oligonucleotide hybridizes to the circular or circularizable probe. In some embodiments, the circularizable probe is circularized (e.g., by target RNA templated ligation) prior to contacting the sample with the primer oligonucleotide, the ribonuclease H (RNase H), and/or the polymerase. The first buffer can be free or substantially free of a cofactor (e.g., a catalytic cation, such as $Mg^{2+}$ and/or $Mn^{2+}$) for the RNase H and the polymerase (e.g., an "OFF" buffer). In some embodiments, the first buffer may comprise a non-catalytic cation, such as $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, the first buffer comprises $Ca^{2+}$. Molecules of the RNase H and the polymerase can be loaded onto the target RNA, the circular or circularized probe, and/or the primer oligonucleotide, but the enzymes do not cleave the target RNA or carries out RCA in the absence of the cofactor. The sample can be incubated in a second buffer comprising the cofactor (e.g., an "ON" buffer), thereby allowing the loaded RNase H molecules to cleave the DNA-annealed target RNA sequence, as well as allowing the polymerase to carry out RCA using the primer oligonucleotide and the RNase H-cleaved target RNA as RCA primers.

In certain aspects, the provided methods comprise a circular probe that hybridizes to a target RNA sequence in a target RNA. In some embodiments, the circular probe is formed by ligating a circularizable probe. In some embodiments, the ligation is a DNA-DNA templated ligation. In some embodiments, the ligation is an RNA-RNA templated ligation. Exemplary RNA-templated ligation probes and methods are described in US 2020/0224244 which is incorporated herein by reference in its entirety. In some embodiments, the ligation is an RNA-DNA templated ligation. In some embodiments, a splint is provided as template for ligation. In some embodiments, the splint comprises a region configured to hybridize to the target RNA sequence. In some embodiments, the splint does not comprise a region configured to hybridize to the target RNA sequence.

In some embodiments, following formation of the circular probe, the sample is contacted with an RNase H. In some embodiments, the circular probe forms a duplex with a target nucleic acid sequence in a target nucleic acid. In some embodiments, the target sequence is a target RNA sequence and the target nucleic acid is a target RNA. In some embodiments, the RNase H cleaves the target RNA at one or more sites in the target RNA sequence to generate a target RNA fragment. In some embodiments, the target RNA fragment is used as a primer for amplification. In some embodiments, the amplifying is achieved by performing rolling circle amplification (RCA). In some embodiments, the RCA comprises a linear RCA. In some embodiments, the RCA comprises a branched RCA. In some embodiments, the RCA comprises a dendritic RCA. In some embodiments, the RCA comprises any combination of the foregoing.

In some embodiments, the RNase H cleaves the target RNA at one or more sites in the target RNA to generate a target RNA fragment. In some embodiments, the target RNA is cleaved at 1, 2, 3, 4, 5, 6, 7, 8, 9, 10, or more sites in the target RNA sequence. In some embodiments, the target RNA is cleaved at no more than 10, 9, 8, 7, 6, 5, 4, 3, 2, or 1 site in the target RNA sequence. In some embodiments, the target RNA is cleaved at no more than 10 sites by the RNase H. In some embodiments, the target RNA is cleaved at no more than 8 sites by the RNase H. In some embodiments, the target RNA is cleaved at between 0-2, 2-4, 4-6, 6-8, 8-10, 0-5, 5-10, or 1-5, sites in the target RNA sequence. In some embodiments, the target RNA sequence is cleaved at only one site.

In some embodiments, the target RNA sequence and the hybridization region of the circular or circularized probe are between about 10 and about 80 nucleotides, such as between about 20 and about 60 nucleotides, or between about 30 and about 50 nucleotides, or about 40 nucleotides in length. In some embodiments, the target RNA sequence is cleaved by the RNase H at no more than 8 sites. In some embodiments, the RNase H cleaves the target RNA to generate a target RNA fragment that is about 4, 5, 6, 7, 8, 9, or 10 nucleotides or longer. In some embodiments, the target RNA fragment comprises a priming RNA sequence that is hybridized to the circular probe or a circularized probe formed by circularizing the circularizable probe. In some embodiments, the target RNA fragment primes an RCA reaction using the circular probe or circularized probe as template.

In certain aspects, during the amplification step, the amplification comprises both a primer oligonucleotide and a target RNA fragment. In some embodiments, the amplification is primed by both an amplification primer oligonucleotide and a target RNA fragment. In some embodiments, the amplification is primed by the primer oligonucleotide or the target RNA fragment. In some embodiments, the amplification is primed by the primer oligonucleotide. In some embodiments, the amplification is primed by the target RNA fragment.

In some embodiments, a washing step is performed to remove any unbound probes, primers, target RNA fragments, RNase H, etc. In some embodiments, the wash is a stringency wash. Washing steps can be performed at any point during the process to remove non-specifically bound probes, probes that have ligated, etc. In some embodiments, a method disclosed herein comprises washing the biological sample subsequent to the contacting with the circular or circularizable probe, the ligating, and/or the contacting with the primer oligonucleotide and/or the RNase H.

In some embodiments, a circularizable probe disclosed herein is ligated then amplified through rolling circle amplification. In some embodiments, the primary probes, such as a circular or circularizable probe or a probe set that comprises a padlock probe, contain one or more barcodes. In some embodiments, the barcodes are bound by detection primary probes, which do not need to be fluorescent, but that include a target-binding portion (e.g., for hybridizing to one or more primary probes) and multiple other barcodes (e.g., secondary barcodes, versus the primary barcodes on the primary probes).

In some embodiments, the method comprises using a circular or circularizable construct hybridized to the nucleic acid of interest to generate a circular nucleic acid. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In some embodiments, the circular nucleic acid is a construct formed using ligation (e.g., as described in Section IV.A.). In some embodiments, the circular construct is formed using template primer extension followed by ligation. In some embodiments, the circular construct is formed by providing an insert between ends to be ligated. In some embodiments, the circular construct is formed using a combination of any of the foregoing.

Following formation of the circular nucleic acid, in some instances, a primer oligonucleotide is added for amplification. In some instances, the primer oligonucleotide for amplification is added with the primary and/or secondary probes. In some instances, the primer oligonucleotide for amplification is added after the primary and/or secondary probes. In some embodiments, the biological sample is first contacted with the RNase H, then contacted with the primer oligonucleotide and the polymerase. In some instances, the primer oligonucleotide for amplification may also be complementary to the target nucleic acid and the circular or circularizable probe. In some embodiments, a washing step is performed to remove any unbound probes, primers, etc. In some embodiments, the wash is a stringency wash. Washing steps can be performed at any point during the process to remove non-specifically bound probes, probes that have ligated, etc.

A primer oligonucleotide (e.g., external primer oligonucleotide) is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. In any of the embodiments herein, a primer extension reaction can be any method where two nucleic acid sequences become linked (e.g., hybridized) by an overlap of their respective terminal complementary nucleic acid sequences (e.g., 3' termini). Such linking can be followed by nucleic acid extension (e.g., an enzymatic extension) of one, or both termini using the other nucleic acid sequence as template for extension. Enzymatic extension can be performed by an enzyme including, but not limited to, a polymerase and/or a reverse transcriptase.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of a circularizable probe or probe set, e.g., a padlock probe) the circular probe is rolling circle amplified to generate an RCA product (e.g., amplicon) containing multiple copies of the circular.

In some embodiments, rolling circle amplification products are generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof. In some embodiments, the polymerase is Phi29 DNA polymerase.

In some embodiments, the polymerase comprises a modified recombinant Phi29-type polymerase. In some embodiments, the polymerase comprises a modified recombinant Phi29, B103, GA-1, PZA, Phi15, BS32, M2Y, Nf, G1, Cp-1, PRD1, PZE, SF5, Cp-5, Cp-7, PR4, PR5, PR722, or L17 polymerase. In some embodiments, the polymerase comprises a modified recombinant DNA polymerase having at least one amino acid substitution or combination of substitutions as compared to a wildtype Phi29 polymerase. Exemplary polymerases are described in U.S. Pat. Nos. 8,257,954; 8,133,672; 8,343,746; 8,658,365; 8,921,086; and 9,279,155, all of which are herein incorporated by reference. In some embodiments, the polymerase is not directly or indirectly immobilized to a substrate, such as a bead or planar substrate (e.g., glass slide), prior to contacting a sample, although the sample may be immobilized on a substrate.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some aspects, during the amplification step, modified nucleotides can be added to the reaction to incorporate the modified nucleotides in the amplification product. Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprise a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some embodiments, the method can further comprise a step of removing molecules of the polymerase and/or the polynucleotide that are not bound to the circular nucleic acid from the biological sample. In some embodiments, the method can further comprise one or more stringency washes between the reagent contacting steps.

In some embodiments, the primer extension reaction mixture can comprise a deoxynucleoside triphosphate (dNTP) or derivative, variant, or analogue thereof. In some embodiments, the primer extension reaction mixture can comprise a catalytic cofactor of the polymerase. In any of the preceding embodiments, the primer extension reaction mixture can comprise a catalytic di-cation, such as $Mg^{2+}$ and/or $Mn^{2+}$. In some embodiments, the primer extension reaction mixture is substantially free of a non-catalytic cation, such as $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, a catalytic cation in the primer extension reaction mixture can replace a non-catalytic cation in complex with the polymerase that is bound to the circular nucleic acid or the RCA primer, thus turning on the polymerase activity of the polymerase. In some embodiments, when the sample is contacted with a primer extension reaction mixture comprising a catalytic di-cation (such as $Mg^{2+}$ and/or $Mn^{2+}$), a non-catalytic cation (such as $Ca^{2+}$, $Zn^{2+}$, $Co^{2+}$, $Ni^{2+}$, $Eu^{2+}$, $Sr^{2+}$, $Ba^{2+}$, $Fe^{2+}$, and/or $Eu^{2+}$) bound to Phi29 is displaced, thereby activating the 5'→3' polymerase activity and the 3'→5' exonuclease (proofreading) activity of Phi29.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, US 2016/0024555, US 2018/0251833, US 2016/0024555, US 2018/0251833 and US 2017/0219465, all of which are herein incorporated by reference in their entireties. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. An RCA-based detection system can be used, e.g., where the signal is provided by generating a RCA product (RCP) from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (e.g., a reagent in a detection assay), which is used as a reporter for the assay, or a part of a reporter, or signal-generation system. The RCA template used to generate the RCP may thus be a circular (e.g., circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

Following amplification, the sequence of the amplicon (e.g., RCA product) or a portion thereof, is determined or otherwise analyzed, for example by using detectably labeled probes and imaging. The sequencing or analysis of the amplification products can comprise sequencing by hybridization, sequencing by ligation, and/or fluorescent in situ sequencing, and/or wherein the in situ hybridization comprises sequential fluorescent in situ hybridization. In some instances, a sequence of the RCA product is detected using, e.g., the secondary and higher order probes and detection oligonucleotides described herein (e.g., in Section V).

V. Detection and Analysis

In some embodiments, a method disclosed herein comprises detecting one or more target nucleic acids (e.g., target RNA) in a sample using a plurality of primary probes (e.g., circular or circularizable probes) configured to hybridize to the one or more target nucleic acids, wherein each primary probe comprises hybridization region configured to hybridize to a different target region in the corresponding target nucleic acid, and a barcode region.

In some embodiments, the sample is contacted with a plurality of detectable probes, wherein each detectable probe is configured to hybridize to a complement of a barcode sequence in the barcode regions of the plurality of primary probes. In some embodiments, the complement of the barcode sequence is present in multiple copies in a nucleic acid concatemer, such as a rolling circle amplification (RCA) product (e.g., generated as described in Section IV.B). In some embodiments, the method further comprises detecting a signal associated with the plurality of detectable probes or absence thereof at one or more locations in the sample. In some embodiments, the sample is contacted with a subsequent plurality of detectable probes, wherein each detectable probe in the subsequent plurality is configured to hybridize to a complement of the subsequent barcode sequence in the barcode regions of the plurality of primary probes. In some embodiments, the complement of the subsequent barcode sequence is present in multiple copies in a nucleic acid concatemer, such as a rolling circle amplification (RCA) product. In some embodiments, the method further comprises detecting a subsequent signal associated with the subsequent plurality of detectable probes or absence thereof at the one or more locations in the sample. In some embodiments, the method further comprises generating a signal code sequence comprising signal codes corresponding to the signal or absence thereof and the subsequent signal or absence thereof, respectively, at the one or more locations, wherein the signal code sequence corresponds to one of the one or more target nucleic acids, thereby identifying the target nucleic acid at the one or more locations in the sample. In some embodiments, the RCA products for multiple target nucleic acids (e.g., target RNA) are generated in the sample, and the RCA products are generated using fragments of the target nucleic acids (e.g., generated by RNase H1 and/or RNase H2 treatment) and/or externally provided DNA oligonucleotides as RCA primers.

In some embodiments, the method comprises generating a signal code sequence at one or more locations in a sample, the signal code sequence comprising signal codes corresponding to the signals (or absence thereof) associated with detectable probes for in situ hybridization that are sequentially applied to the sample, wherein the signal code sequence corresponds to an analyte in the sample, thereby detecting the analyte at the one or more of the multiple locations in the sample.

In some embodiments, a method disclosed herein comprises generating rolling circle amplification (RCA) products associated with one or more target nucleic acids (e.g., target RNA) in a sample. In some embodiments, the RCA products are detected in situ in a sample, thereby detecting the one or more target nucleic acids. In some embodiments, each of the RCA products comprises multiple complementary copies of a barcode sequence, wherein the barcode sequence is associated with a target nucleic acid in the sample and is assigned a signal code sequence. In some embodiments, the method comprises contacting the sample with a first detectable probe comprising (i) a recognition sequence complementary to a sequence in the complementary copies of the barcode sequence and (ii) a reporter. In some embodiments, the method comprises detecting a first signal or absence thereof from the reporter of the first detectable probe hybridized to its corresponding sequence of the complementary copies of the barcode sequence in the RCA product, wherein the first signal or absence thereof corresponds to a first signal code in the signal code sequence. In some embodiments, the method comprises contacting the sample with a subsequent detectable probe comprising (i) a recognition sequence complementary to a sequence of the complementary copies of the barcode sequence and (ii) a reporter. In some embodiments, the method comprises detecting a subsequent signal or absence thereof from the reporter of the subsequent detectable probe hybridized to its corresponding sequence of the complementary copies of the barcode sequence in the RCA product, wherein the subsequent signal or absence thereof corresponds to a subsequent signal code in the signal code sequence. In some embodiments, the signal code sequence comprising the first signal code and the subsequent signal code is determined at a location in the sample, thereby decoding the barcode sequence and identifying the target nucleic acid (e.g., target RNA) at the location in the sample. In some embodiments, the RCA products for multiple target nucleic acids (e.g., target RNA) are generated in the sample, and the RCA products are generated using fragments of the target nucleic acids (e.g., generated by RNase H1 and/or RNase H2 treatment) and externally provided DNA oligonucleotides as RCA primers.

The recognition sequences may be of any length, and multiple recognition sequences in the same or different secondary nucleic acid probes may be of the same or different lengths. If more than one recognition sequence is used, the recognition sequences may independently have the same or different lengths. For instance, the recognition sequence may be at least 4, at least 5, least 6, least 7, least 8, least 9, at least 10, least 11, least 12, least 13, least 14, at least 15, least 16, least 17, least 18, least 19, at least 20, at least 25, at least 30, at least 35, at least 40, or at least 50 nucleotides in length. In some embodiments, the recognition sequence may be no more than 48, no more than 40, no more than 32, no more than 24, no more than 16, no more than 12, no more than 10, no more than 8, or no more than 6 nucleotides in length. Combinations of any of these are also possible, e.g., the recognition sequence may have a length of between 5 and 8, between 6 and 12, or between 7 and 15 nucleotides, etc. In one embodiment, the recognition sequence is of the same length as a barcode sequence or complement thereof of a primary nucleic acid probe or a product thereof. In some embodiments, the recognition sequence may be at least 50%, at least 60%, at least 70%, at least 75%, at least 80%, at least 85%, at least 90%, at least 92%, at least 94%, at least 95%, at least 96%, at least 97%, at least 98%, at least 99%, or at least 100% complementary to the barcode sequence or complement thereof.

In some embodiments, the barcode sequence comprises one or more barcode positions each comprising one or more barcode subunits. In some embodiments, a barcode position in the barcode sequence partially overlaps an adjacent barcode position in the barcode sequence. In some embodiments, the first detectable probe and the subsequent detectable probe are in a set of detectable probes each comprising the same recognition sequence and a reporter. In some embodiments, the reporter of each detectable probe in the set comprises a binding site for a reporter probe comprising a detectable moiety. In some embodiments, the reporter probe binding site of the first detectable probe and the reporter probe binding site of the subsequent detectable probe are the same. In some embodiments, the reporter probe binding site of the first detectable probe and the reporter probe binding site of the subsequent detectable probe are different. In some embodiments, the detectable moiety is a fluorophore and the signal code sequence is a fluorophore sequence uniquely assigned to the target nucleic acid (e.g., target RNA). In some embodiments, the detectable probes in the set are contacted with the sample sequentially in a pre-determined sequence which corresponds to the signal code sequence assigned to the barcode sequence. In some embodiments, the detectable probes in the set are contacted with the sample to determine signal codes in the signal code sequence until sufficient signal codes have been determined to decode the barcode sequence, thereby identifying the target nucleic acid (e.g., target RNA).

In some aspects, the provided methods involve analyzing, e.g., detecting or determining, one or more sequences present in the polynucleotides and/or in a product or derivative thereof, such as in an amplified circularizable probe or probe set (e.g., padlock probe). In some cases, the analysis is performed on one or more images captured, and may comprise processing the image(s) and/or quantifying signals observed. For example, the analysis may comprise processing information of one or more cell types, one or more types of biomarkers, a number or level of a biomarker, and/or a number or level of cells detected in a particular region of the sample. In some embodiments, the analysis comprises detecting a sequence e.g., a barcode present in the sample. In some embodiments, the analysis includes quantification of puncta (e.g., if amplification products are detected). In some cases, the analysis includes determining whether particular cells and/or signals are present that correlate with one or more biomarkers from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

In any of the embodiments herein, a sequence associated with the target nucleic acid or the circular probe(s) can comprise one or more barcode sequences or complements thereof. In any of the embodiments herein, the sequence of the rolling circle amplification product can comprise one or more barcode sequences or complements thereof. In any of the embodiments herein, a circular or circularizable probe can comprise one or more barcode sequences or complements thereof. In any of the embodiments herein, the one or more barcode sequences can comprise a barcode sequence corresponding to the target nucleic acid. In any of the embodiments herein, the one or more barcode sequences can comprise a barcode sequence corresponding to the sequence of interest, such as variant(s) of a single nucleotide of interest.

In some embodiments, a nucleic acid probe, such as a primary or a secondary nucleic acid probe, may also comprise 1, 2, 3, 4, 5, 6, 7, 8, 9, 10, 11, 12, 13, 14, 15 or more, 20 or more, 32 or more, 40 or more, or 50 or more barcode sequences. The barcode sequences may be positioned anywhere within the nucleic acid probe. If more than one barcode sequences are present, the barcode sequences may be positioned next to each other, and/or interspersed with other sequences. In some embodiments, two or more of the barcode sequences may also at least partially overlap. In some embodiments, two or more of the barcode sequences in the same probe do not overlap. In some embodiments, all of the barcode sequences in the same probe are separated from one another by at least a phosphodiester bond (e.g., they may be immediately adjacent to each other but do not overlap), such as 1, 2, 3, 4, 5, 6, 7, 8, 9, 10 or more nucleotides apart.

The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In any of the embodiments herein, the detecting step can comprise contacting the biological sample with one or more detectably labeled probes that directly or indirectly hybridize to the rolling circle amplification product, and dehybridizing the one or more detectably labeled probes from the rolling circle amplification product. In any of the embodiments herein, the contacting and dehybridizing steps can be repeated with the one or more detectably labeled probes and/or one or more other detectably labeled probes that directly or indirectly hybridize to the rolling circle amplification product.

In any of the embodiments herein, the detecting step can comprise contacting the biological sample with one or more intermediate probes that directly or indirectly hybridize to the rolling circle amplification product, wherein the one or more intermediate probes are detectable using one or more detectably labeled probes. In any of the embodiments herein, the detecting step can further comprise dehybridizing the one or more intermediate probes and/or the one or more detectably labeled probes from the rolling circle amplification product. In any of the embodiments herein, the contacting and dehybridizing steps can be repeated with the one or more intermediate probes, the one or more detectably labeled probes, one or more other intermediate probes, and/or one or more other detectably labeled probes.

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the primary probes, secondary probes, higher order probes, and/or detectably labeled probes may comprise any of a variety of entities able to hybridize a nucleic acid, e.g., DNA, RNA, LNA, and/or PNA, etc., depending on the application.

In some embodiments, a method disclosed herein may also comprise one or more signal amplification components. In some embodiments, the present disclosure relates to the detection of nucleic acids sequences in situ using probe hybridization and generation of amplified signals associated with the probes (e.g., using RCA), wherein background signal is reduced and sensitivity is increased.

In some embodiments, the methods comprise detecting the sequence of all or a portion of the amplification product, such as one or more barcode sequences present in the amplification product.

In some embodiments, the analysis and/or sequence determination comprises detecting all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the polynucleotides, for example, via binding of the detection probe and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to fluorophores phycoerythrin, ALEXA FLUOR™ dyes, fluorescein, YPet, CyPet, Cascade blue, allophycocyanin, Cy3®, Cy5®, Cy7®, rhodamine, dansyl, umbelliferone, TEXAS RED™, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (Max Vision Biosciences), and/or a very intense black dye (e.g., Sudan Black, or comparable dark chromophore).

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519, all of which are herein incorporated by reference in their entireties. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes), all of which are herein incorporated by reference in their entireties. Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/

0017264, all of which are herein incorporated by reference in their entireties. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3®-dCTP, Cy3®-dUTP, Cy5®-dCTP, Cy5®-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.).

Other fluorophores available for post-synthetic attachment comprise, but are not limited to, fluorophores ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, TEXAS RED™ (available from Molecular Probes, Inc., Eugene, Oreg.), Cy2®, Cy3.5®, Cy5.5®, and Cy7® (Amersham Biosciences, Piscataway, N.J.). FRET tandem fluorophores may also be used, comprising, but not limited to, PerCP-Cy5.5®, PE-Cy5®, PE-Cy5.5®, PE-Cy78, PE-TEXAS RED™, APC-Cy7R, PE-ALEXA FLUOR™ dyes (610, 647, 680), and APC-ALEXA FLUOR™ dyes.

In some cases, metallic silver or gold particles may be used to enhance signal from fluorescently labeled nucleotide and/or polynucleotide sequences [Lakowicz et al. (2003) Bio Techniques 34:62].

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In any of the embodiments herein, an antibody can be an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or a polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, all of which are herein incorporated by reference in their entireties, and PCT publication WO 91/17160. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a simpler set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity, so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large, clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECS™), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing or sequence detection can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363. In addition, examples of methods and systems for performing in situ sequencing are described in US 2016/0024555, US 2019/0194709, and in U.S. Pat. Nos. 10,138,509, 10,494,662 and 10,179,932, all of which are herein incorporated by reference in their entireties. Exemplary techniques for in situ sequencing comprise, but are not limited to, STARmap (described for example in Wang et al., (2018) *Science,* 361(6499) 5691), MERFISH (described for example in Moffitt, (2016) *Methods in Enzymology,* 572, 1-49), hybridization-based in situ sequencing (HybISS) (described for example in Gyllborg et al., Nucleic Acids Res (2020) 48(19):e112, and FISSEQ (described for example in US 2019/0032121). In some cases, sequencing can be performed after the analytes are released from the biological sample.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232, all of which are herein incorporated by reference in their entireties.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

VI. Compositions and Kits

Also provided herein are kits, for example comprising one or more oligonucleotides disclosed herein, and reagents for performing the methods provided herein, for example reagents required for one or more steps comprising hybridization, ligation, amplification (e.g., primer oligonucleotides, ribonuclease H (RNase H), and polymerases), detection, and/or sample preparation as described herein. In some embodiments, the kit comprises one or more reagents such as buffers for performing rolling circle amplification (e.g., crowding agents) as described in Section IV. In some embodiments, the kit further comprises a target nucleic acid. In some embodiments, any or all of the polynucleotides are DNA molecules. In some embodiments, the target nucleic acid is a messenger RNA molecule.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

In some aspects, the provided embodiments can be applied in an in situ method of analyzing nucleic acid sequences, such as an in situ transcriptomic analysis, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

VII. Applications

In some aspects, the provided methods can be applied to detect, image, quantitate, or determine the presence or absence of one or more target nucleic acid(s) or portions thereof (e.g., presence or absence of sequence variants such as point mutations and SNPs). In some aspects, the provided methods can be applied to detect, image, quantitate, or determine the sequence of one or more target nucleic acid(s), comprising sequence variants such as point mutations and SNPs.

In some aspects, the provided embodiments can be employed for in situ detection and/or sequencing of a target nucleic acid in a cell, e.g., in cells of a biological sample or a sample derived from a biological sample, such as a tissue section on a solid support, such as on a transparent slide. In some aspects, the target nucleic acid molecule is an RNA. In some aspects, the nucleic acid molecule is linear or circular (e.g., a linear RNA or a circular RNA). In further aspects, the target nucleic acid molecule is an mRNA, which can include, but is not limited to, a nascent RNA, a pre-mRNA, a primary-transcript RNA, a processed RNA, a capped mRNA, a non-capped mRNA, a polyadenylated mRNA, a non-polyadenylated mRNA, a spliced mRNA, or a non-spliced mRNA. In a further aspect, the target nucleic acid is non-coding RNA (ncRNA), which can include, but is not limited to a tRNA, tsRNA, rRNA, srRNA, miRNA, siRNA, piRNA, snoRNA, snRNA, exRNA, scaRNA, gRNA, or long ncRNA (lncRNA), optionally wherein the lncRNA is Xist or HOTAIR. In some aspects, the target nucleic acid molecule is a viral, bacterial, fungal, plant, mammalian, or synthetic nucleic acid.

In some aspects, the provided methods involve a step of contacting, or hybridizing, one or more polynucleotides, such as the probe described herein, to a cell or a sample containing the target nucleic acid molecule with a region of interest in order to form a hybridization complex. A nucleic acid probe typically contains a sequence (e.g., hybridization region) that is able to directly or indirectly bind to at least a portion of a target nucleic acid molecule. The nucleic acid probe may be able to bind to a specific target nucleic acid (e.g., an mRNA or a ncRNA).

In some aspects, the methods provided herein comprise one or more stringent wash steps in order to remove the unbound and/or nonspecifically bound circular probes from the sample. In some aspects, the removal of the unbound and/or nonspecifically bound probes may serve to increase the sensitivity and specificity of signal detection. In some aspects, the signal detected is associated with the circular probe or a product thereof generated without de-circularizing the circular probe In some aspects, the provided embodiments can be applied in an in situ method of analyzing nucleic acid sequences, such as an in situ transcriptomic analysis, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some embodiments, the region of interest comprises a single-nucleotide polymorphism (SNP). In some embodiments, the region of interest comprises is a single-nucleotide variant (SNV). In some embodiments, the region of interest comprises a single-nucleotide substitution. In some embodiments, the region of interest comprises a point mutation. In some embodiments, the region of interest comprises a single-nucleotide insertion.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

VIII. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a bead, and/or a probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution. In some embodiments, a barcode includes a UMI. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as template for replication of a particular nucleotide sequence. Naturally occurring nucleic acids generally have a backbone containing phosphodiester bonds. An analog structure can have an alternate backbone linkage. Naturally occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G).

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

Two nucleic acid sequences may become linked (e.g., hybridized) by an overlap of their respective terminal complementary nucleic acid sequences (e.g., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as template for nucleic acid synthesis. Similarly, a 3' polyadenylated tail of an mRNA transcript that hybridizes to a poly (dT) sequence (e.g., capture domain) can be used as template for single-strand synthesis of a corresponding cDNA molecule.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus.*

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally occurring enzymes but also all modified derivatives thereof, also including derivatives of naturally occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g., DNA polymerase activity of the wild-type sequence. Mutations can affect the activity profile of the enzymes, e.g., enhance or reduce the rate of polymerization, under different reaction conditions, e.g., temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g., sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g., reverse transcriptase, activity of the wild-type sequence. The reverse transcriptase enzyme can be provided as part of a composition that includes other components, e.g., stabilizing components that enhance or improve the activity of the reverse transcriptase enzyme, such as RNase inhibitor(s), inhibitors of DNA-dependent DNA synthesis, e.g., actinomycin D. Many sequence-modified derivative or mutants of reverse transcriptase enzymes, e.g., M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g., Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as template. Thus, in some embodiments, the reverse transcription reaction can use an enzyme (reverse transcriptase) that is capable of using both RNA and ssDNA as the template for an extension reaction, e.g., an AMV or MMLV reverse transcriptase.

In some embodiments, the quantification of RNA and/or DNA is carried out by real-time PCR (also known as quantitative PCR or qPCR), such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature or composition to be detected. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. For example, the fluorophore can be from a group that includes: fluorophores 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18 (3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), Lyso Tracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-TEXAS RED™, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5®), Quinacrine Mustard, R670 (PE-Cy5®), Red 613 (PE-TEXAS RED™), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARFR-1 (low pH), Sodium Green™, SpectrumAqua®, SpectrumGreen® #1, SpectrumGreen® #2, SpectrumOrange®, SpectrumRed®, SYTOR 11, SYTOR 13, SYTO® 17, SYTOR 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5®), TRITC (Tetramethylrhodamine), TruRed (PerCP-Cy5.5®), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow®, MAX, TET, TEX615, ATTO™ 488, ATTO™ 532, ATTO™ 550, ATTO™ 565, ATTO™ Rho101, ATTO™ 590, ATTO™ 633, ATTO™ 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families can provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLE

The following examples are included for illustrative purposes only and are not intended to limit the scope of the present disclosure.

Example 1: In Vitro Testing of RNase H Assisted RCA

This example describes the use of RNase H to assist with rolling circle amplification (RCA). The general strategy for RNase H assisted priming using a circular or circularizable probe (e.g., padlock probe) is shown in FIG. 1A. Briefly, circular or circularizable probes are hybridized to a target RNA molecule and the probe is ligated using the target RNA molecule as template. The sample is then contacted with RNase H, and the RNase H-treated sample is subjected to RCA using the Phi29 polymerase. The RNase H creates nicks in the target RNA molecule in the target RNA/circular or circularized probe duplex, which generates a target RNA fragment that can serve as a primer for Phi29 in RCA. RCA products are then detected using SYBR gold labeling.

Figure 2:
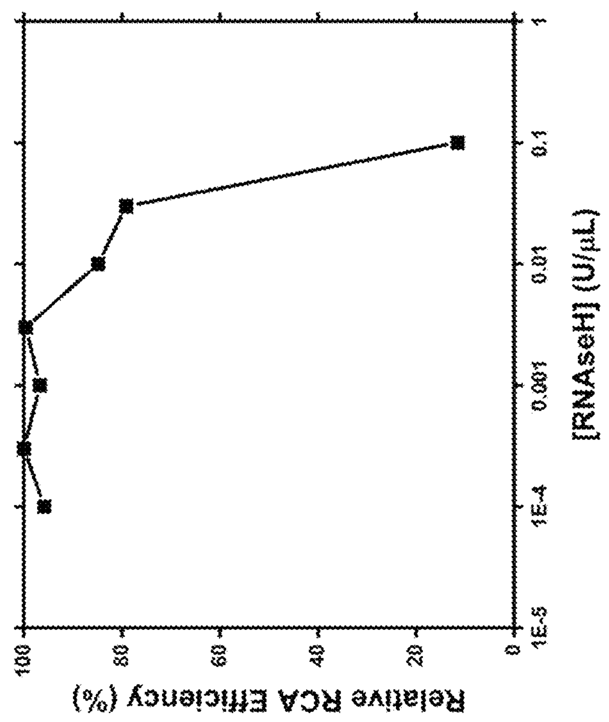
FIG. 2 shows the results in Fluorescence (AU) and Relative RCA Efficiency (%) of an in vitro RNase H assisted RCA reaction using different RNase H concentrations.
Figure 2:
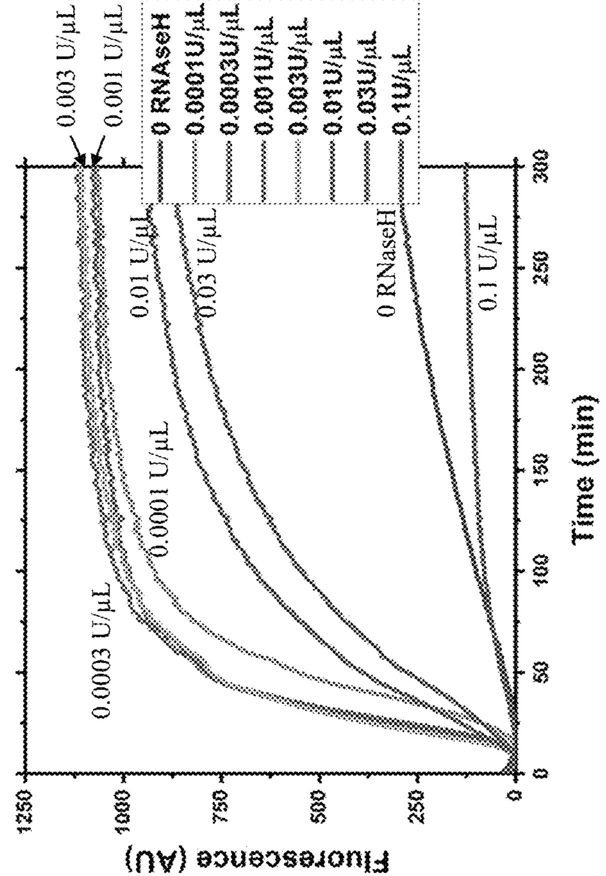

FIG. 2 shows the results of RNase H assisted RCA performed in vitro using different concentrations of RNase H catalytic activity (U/μL). In FIG. 2, left panel, Fluorescence (AU) of SYBR gold signals observed in products of RCA reactions using different RNase H concentrations between 0.0001 U/μL and 0.03 U/μL were higher than that in the control group (no RNase treatment) and in the 0.1 U/μL RNase H group. FIG. 2, right panel, shows the Relative RCA Efficiency (%) of the in vitro RNase H assisted RCA, showing RCA reactions using lower RNase H concentrations performed more efficiently than high RNase H concentrations (e.g., above approximately 0.01 U/μL), with the greatest RCA efficiencies observed in reactions using between 0.0001 U/μL and 0.003 U/L RNase H. These results demonstrate that RNase H can be used to facilitate RCA reactions, increase signal intensity of RCA products, and/or improve RCA efficiency.

Example 2: In Situ Detection of RNA Using RNase H Assisted RCA

In this example, the sensitivity of detecting mRNAs in situ using RNase H assisted RCA was assessed.

Detection of Satb2 and Prox1 was performed on mouse brain tissue samples. Padlock probes for Satb2 and Prox1 were added to the sample and allowed to hybridize. Samples were washed to remove unbound probe. For padlock probe ligation, ligation reaction mix, including SplintR® ligase buffer and SplintR® DNA ligase, was added to the sample.

For RCA, samples were incubated in a reaction mix containing Phi29 polymerase buffer, dNTPs, and Phi29 polymerase. RCA reactions were performed using either a control primer alone, RNase H treatment alone, or with no primer and no RNase H treatment. RCA products (RCP) were detected by hybridizing labeled probes to the RCPs in situ and imaging samples with a fluorescent microscope.

Figure 3A:
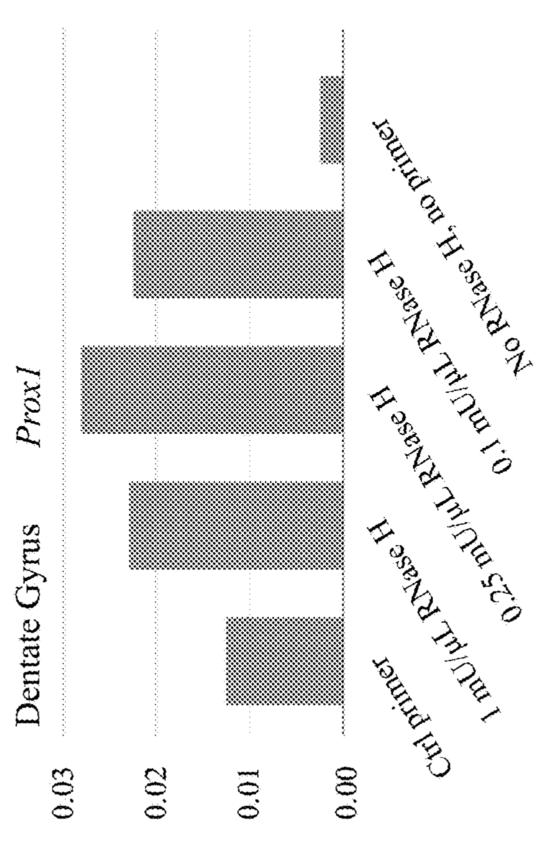
FIGS. 3A-3B show results for exemplary methods of detecting mRNA using RNase H assisted RCA.
Figure 3A:
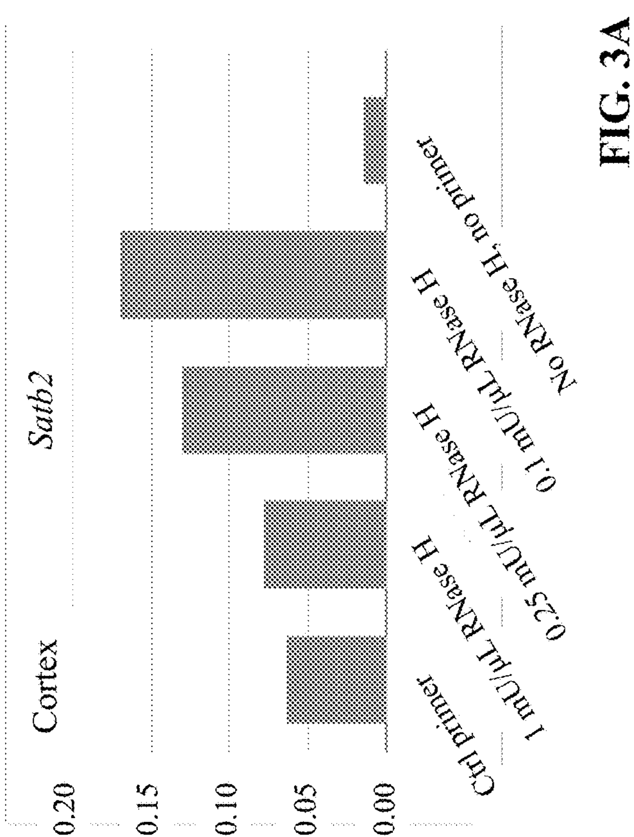
Figure 3B:
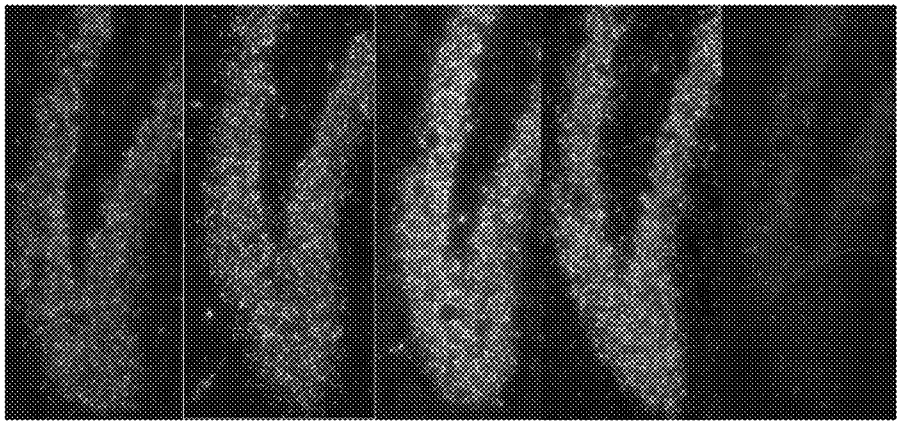

FIGS. 3A-3B show the normalized sequence density and a tissue sample of RCA performed with either a control primer, 1 mU/μL RNase H treatment, 0.25 mU/μL RNase H treatment, 0.1 mU/μL RNase H treatment, or no RNase H treatment and no primer. For each RNase H activity condition tested, the normalized signal density was greater than that of the control primer alone, indicating greater initiation efficiency of RCA in RNase H treated samples than in samples using an external DNA primer (FIG. 3A). FIG. 3B shows a representative image of in situ detection of Prox1 in mouse dentate gyrus. These results indicate that RNase H assisted direct RNA detection using RCA is more sensitive than RCA with an external DNA primer.

To further assess RNase H assisted RCA in situ, additional experiments were conducted using both an external DNA primer and RNase H treatment for the RCA reactions. Experiments were performed similarly as above, using padlock probes to detect Satb2 and Prox1 in mouse brain tissue samples.

Figure 4:
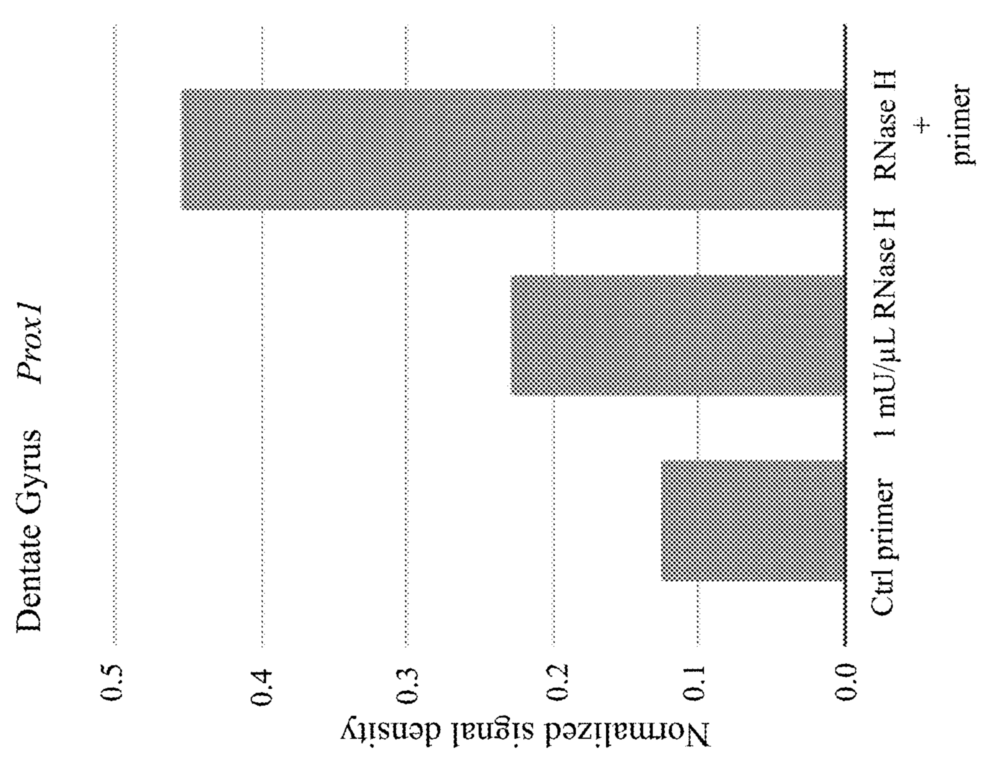
FIG. 4 shows the results in normalized signal density for exemplary methods of detecting mRNA using RNase H together with an external RCA primer (control primer), showing greater sensitivity when both the RCA primer and RNase H treatment were used, compared to using the RCA primer or RNase H treatment alone.
Figure 4:
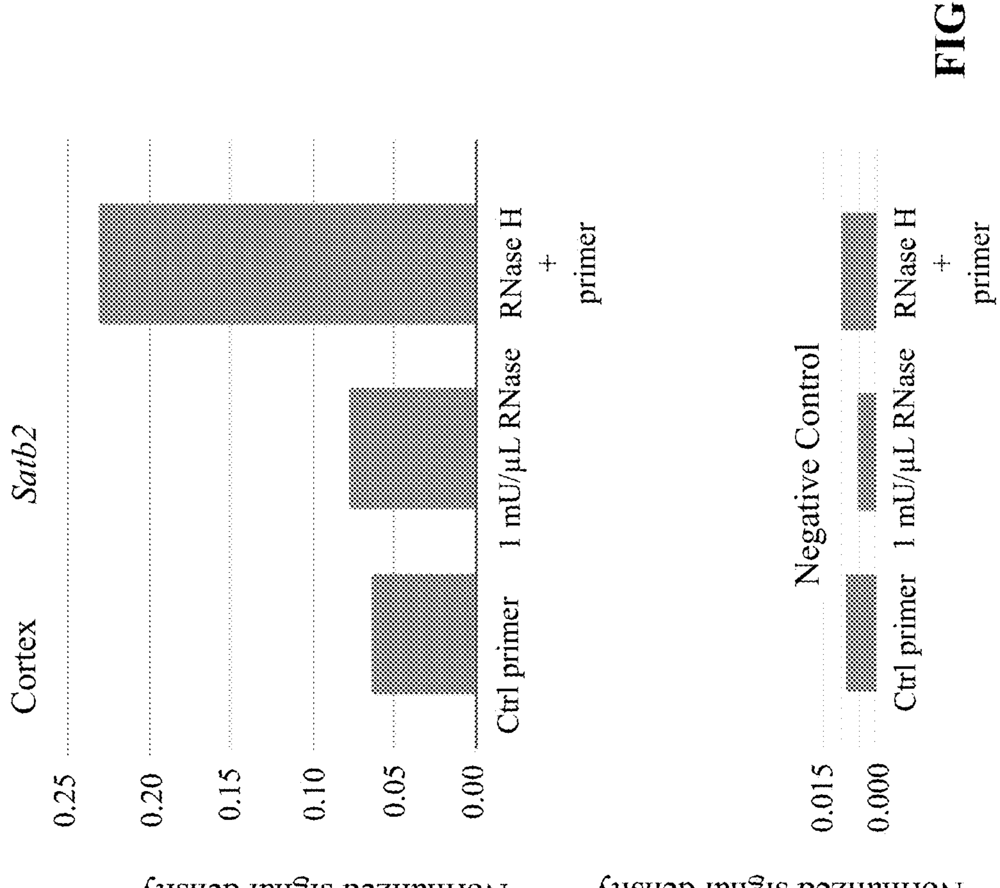

FIG. 4 shows the normalized signal density of RCA performed using the primer alone (control primer), 0.1 mU/μL RNase H treatment alone, or both the primer and RNase H treatment. While either the primer or the RNase H treatment alone generated RCA products, a synergistic effect in normalized signal density of the RCA products was observed when both an external primer and RNase H treatment were used together for RCA, with the normalized signal density being higher than either the control primer or the RNase H treatment group alone. Results for Satb2 signals in the cortex and Prox1 signals in the dentate gyrus in mouse brain tissue samples are shown in FIG. 4. In the negative control group, the negative control padlock probes were known to not bind any target RNA in the mouse brain samples. The results show that RNase H treatment did not decrease the specificity of the RCA-base assay or cause significant off target RCA product generation. These results indicate that performing RCA using both a primer and RNase H could improve sensitivity without losing specificity and reduce performance variability of RCA in different sample types, as compared to primer or RNase H alone.

Example 3: In Situ Detection of RNA Using RNase H Assisted RCA with Activation In this example, the sensitivity of detecting mRNAs in situ using RNase H assisted RCA was further assessed. In some instances, it was observed that RNase H treatment may cause nonspecific cutting of RNA strand, potentially resulting in RCA products (RCPs) diffusing away from an original location. A condition was provided to treat the sample with RNase H in an "OFF" buffer (50 mM Tris-Cl, pH 8.3, 75 mM KCl, and 10 mM DTT) that only allows RNase H to bind to the substrate but not to activate its activity. Then, after RNase H binding, excess/non-bound RNase H molecules were washed away, the RNase H nicking activity was activated, simultaneously allowing the RCA reaction to start in the "ON" buffer (50 mM Tris-Cl, pH 8.3, 10 mM $MgCl_2$, 10 mM ammonium sulfate, 4 mM DTT, and 0.2 mM dNTPs). The sensitivity of detecting mRNAs in situ using RNase H assisted RCA was assessed under various conditions provided in Table 1.

TABLE 1

RNase H assisted Activation and RCA Conditions

| Condition | RCA primer | RNase H | [RNase H] | Order |
|---|---|---|---|---|
| 1 | + | − | − | Only RCA primer was added |
| 2 | + | + | 1 mU/μL | RNase H and RCA primer were both added same time to start the RCA reaction after padlock probe ligation in "ON" buffer |

TABLE 1-continued

| RNase H assisted Activation and RCA Conditions | | | | |
|---|---|---|---|---|
| Condition | RCA primer | RNase H | [RNase H] | Order |
| 3 | + | + | 1 mU/μL | RNase H was added before RCA reaction in "OFF" buffer for 30 mins incubation at 4° C., and RNase H was washed away with 1xPBS + 0.05% Tween before RCA reaction; RCA primer added with "ON" buffer and polymerase after RNase H wash |
| 4 | + | + | 0.3 mU/μL | RNase H was added before RCA reaction in "OFF" buffer for 30 mins incubation at 4° C., and RNase H was washed away with 1xPBS + 0.05% Tween before RCA reaction; RCA primer added with "ON" buffer and polymerase after RNaseH wash |

Figure 5A:
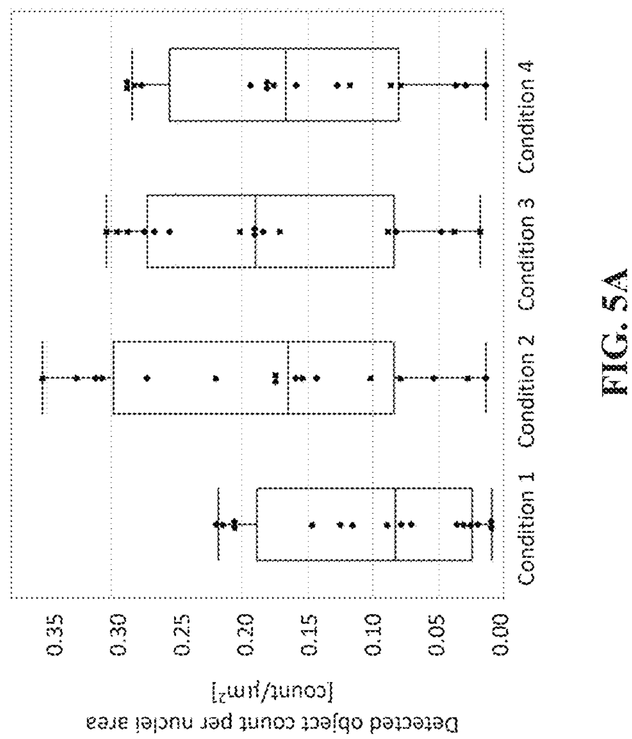
FIGS. 5A-5C show the results for exemplary methods of detecting mRNA using RNase H together with an external RCA primer under various conditions, provided in Table 1.
Figure 5B:
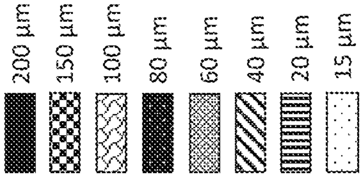
Figure 5B:
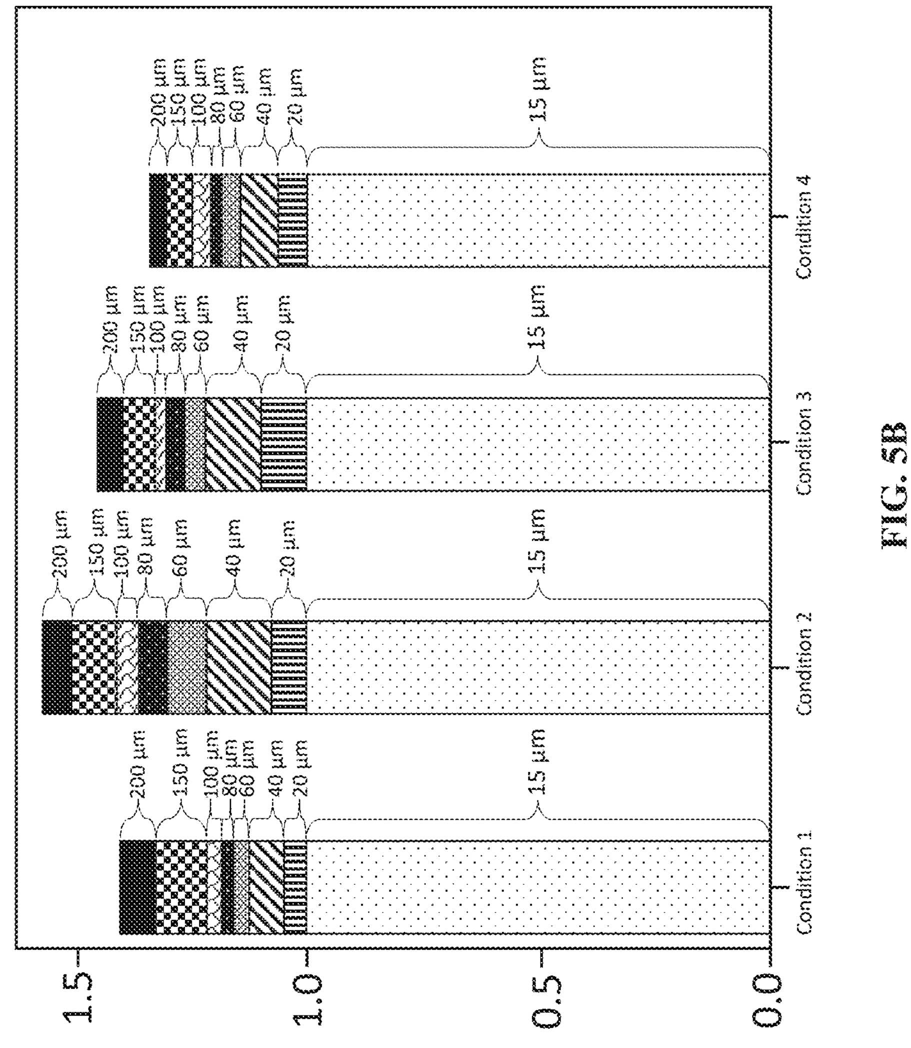
Figure 5C:
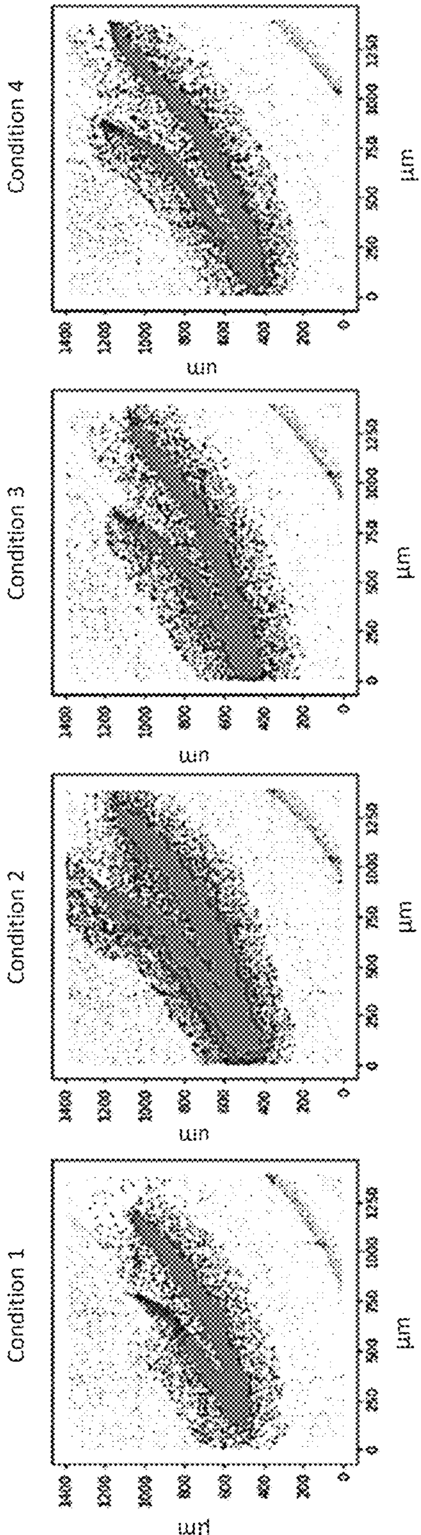

Detection of Prox1 was performed on mouse brain tissue samples. Padlock probes for Prox1 were added to the sample and allowed to hybridize. Samples were washed to remove unbound probe. For padlock probe ligation, ligation reaction mix, including SplintR® ligase buffer and SplintR® DNA ligase, was added to the sample. RCA reactions were then performed in the order described in Table 1. RCPs were detected by hybridizing labeled probes to the RCPs in situ and imaging samples with a fluorescent microscope. As shown in FIG. 5A, the benefit of increased sensitivity by providing RNase H and an external primer was maintained when RNase H was provided in an "OFF" buffer. In FIG. 5B, the normalized ratio of RCP density within indicated distance from nucleic is shown (where the RCP density within 15 μm distance from nuclei is considered as 1 on the y-axis). FIG. 5C shows RCP detected objects for Prox1 at the different distances from Dentate Gyrus nuclei. Potential RCP diffusion was addressed with pre-RNase H treatment as shown in FIGS. 5B-5C where a greater number of Prox1 signals were detected at greater distances from Dentate Gyrus nuclei in Condition 2 as compared to Conditions 3 and 4 which utilized an "OFF" buffer treatment to prevent nonspecific cutting of RNA strands and/or diffusion.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a biological sample, comprising:

(a) contacting the biological sample with a circular or circularizable probe, wherein the circular or circularizable probe comprises a hybridization region that hybridizes to a target RNA sequence in a target RNA in the biological sample to form a duplex, (b) contacting the biological sample comprising the target RNA hybridized to the circular or circularizable probe with a primer oligonucleotide, a ribonuclease H (RNase H), and a polymerase, wherein the primer oligonucleotide comprises a sequence complementary to a sequence in the circular or circularizable probe, and the RNase H cleaves the target RNA in the duplex at one or more sites in the target RNA sequence;

(c) performing rolling circle amplification (RCA) using the circular probe or a circularized probe formed by circularizing the circularizable probe as an RCA template; and (d) detecting one or more products of the RCA, thereby detecting the target RNA or a sequence thereof in the biological sample.

2. The method of claim 1, wherein the method comprises ligating the circularizable probe to form the circularized probe and performing the RCA using the circularized probe as the RCA template.

3. The method of claim 2, wherein the ligating is performed using the target RNA sequence as a ligation template.

4. The method of claim 2, wherein the ligating is performed prior to contacting the biological sample with the RNase H.

5. The method of claim 1, wherein the biological sample is contacted with the primer oligonucleotide, the RNase H, and the polymerase simultaneously.

6. The method of claim 1, wherein the biological sample is contacted with the RNase H prior to contacting the biological sample with the primer oligonucleotide and the polymerase.

7. The method of claim 1, wherein the biological sample is contacted with the RNase H prior to contacting the biological sample with the polymerase.

8. The method of claim 1, wherein the polymerase is a Phi29 DNA polymerase or a Bst DNA polymerase.

9. The method of claim 1, wherein the RNase is an RNase H1 or an RNase H2.

10. The method of claim 1, wherein (b) comprises: contacting the biological sample with the RNase H in a first buffer that is free or substantially free of a cofactor for the RNase H, followed by incubating the biological sample with the RNase H and the cofactor.

11. The method of claim 10, further comprising:

incubating the biological sample with the RNase H in the first buffer, thereby allowing the RNase H to bind the target RNA, the circular or circularizable probe, or the duplex;

removing excess RNase H from the biological sample; and incubating the biological sample in a second buffer which comprises the RNase H and the cofactor, thereby allowing the RNase H to cleave at the one or more sites in the target RNA sequence.

12. The method of claim 1, wherein the one or more products of the RCA comprise an RCA product generated by using the primer oligonucleotide as a primer.

13. The method of claim 1, wherein the biological sample is contacted with the RNase H at a concentration of between about $1\times10^{-3}$ U/μL and about $2\times10^{-2}$ U/μL.

14. The method of claim 1, wherein the detecting comprises contacting the one or more RCA products with a plurality of detectable probes in sequential cycles.

15. A method for analyzing a biological sample, comprising:

(a) contacting the biological sample with a circularizable probe comprising a hybridization region that hybridizes to a target RNA sequence in a target RNA in the biological sample to form a duplex, (b) ligating the circularizable probe to form a circularized probe;

(c) contacting the biological sample comprising the target RNA hybridized to the circularized probe with (i) a primer oligonucleotide that comprises a sequence complementary to a sequence in the circularized probe, (ii) a ribonuclease H (RNase H), and (iii) a Phi29 DNA polymerase, wherein the contacting comprises contacting the biological sample with the RNase H in a first buffer that is free or substantially free of a cofactor for the RNase H, followed by incubating the biological sample in a second buffer comprising the RNase H and the cofactor;

(d) performing rolling circle amplification (RCA) using the circularized probe as an RCA template; and (e) detecting one or more products of the RCA, thereby detecting the target RNA or a sequence thereof in the biological sample.

16. The method of claim 10, wherein the cofactor for the RNase H is $Mg^{2+}$.

17. The method of claim 1, wherein the biological sample is a cell or tissue sample.

18. The method of claim 17, wherein the one or more products of the RCA are detected at location(s) in the biological sample immobilized on a solid support.

19. The method of claim 1, wherein the detecting comprises contacting the one or more RCA products with a plurality of intermediate probes each comprising: (i) a sequence that hybridizes to the one or more RCA products and (ii) a sequence that hybridizes to one or more detectable probes.

* * * * *